United States Patent
Walsh et al.

(10) Patent No.: US 6,218,129 B1
(45) Date of Patent: Apr. 17, 2001

(54) INFLAMMATORY BOWEL DISEASE FIRST STEP ASSAY SYSTEM

(75) Inventors: Michael J. Walsh, San Diego; Steven L. Rose, Escondido, both of CA (US)

(73) Assignee: Prometheus Laboratories, Inc., San Diego, CA (US)

( * ) Notice: Subject to any disclaimer, the term of this patent is extended or adjusted under 35 U.S.C. 154(b) by 0 days.

(21) Appl. No.: 09/079,435

(22) Filed: May 15, 1998

(51) Int. Cl.[7] .................................................. G01N 33/564
(52) U.S. Cl. ........................ 435/7.21; 435/7.24; 435/7.95; 435/7.31; 436/506; 436/513
(58) Field of Search .................................. 435/7.21, 7.24, 435/7.95, 7.31; 436/506, 573

(56) References Cited

PUBLICATIONS

Barnes et al., "Serum Antibodies Reactive with *Saccharomyces cerevisiae* in Inflammatory Bowl Disease: Is IgA Antibody a Marker for Crohn's Disease?," *Int. Arch. Allergy Appl. Immunol.* 92:9–15 (1990).

Brokroelofs et al., "Anti–Neutrophil Cytoplasmic Antibodies (ANCA) in Sera from Patients with Inflammatory Bowel Disease (IBD) Relation to Disease Pattern and Disease Activity," *Digestive Diseases and Sciences* 39:545–549 (1994).

Cambridge et al., "Anti–neutrophil antibodies in inflammatory bowl disease: prevalence and diagnostic role," *Gut* 33:668–674 (1992).

Faille et al., "Evaluation of an Enzyme Immunoassay Using Neoglycolipids Constructed from *Candida albicans* Oligomannosides to Define the Specificity of Anti–Mannan Antibodies," *Eur. J. Clin. Microbiol. Infect. Dis.* 11:438–446 (1992).

Giaffer et al., "Antibodies to *Saccharomyces cerevisiae* in patients with Crohn's disease and their possible pathogenic importance," *Gut* 33:1071–1075 (1992).

Lindberg et al., "Antibody (IgA, IgA, and IgM) to baker's yeast (*Saccharomyces cerevisiae*), yeast mannan, gliadin, ovalbumin and betalactoglobulin in monozygotic twins with inflammatory bowl disease," *Gut* 33:909–913 (1992).

Main et al., "Antibody to *Saccharomyces cerevisiae* (baker's yeast) in Crohn's disease," *British Medical Journal* 297:1105–1106 (1988).

McKenzie et al., "Antibody to selected strains of *Saccharomyces cerevisiae* (baker's and brewer's yeast) and *Candida albicans* in Crohn's disease," *Gut* 31:536–538 (1990).

McKenzie et al., "Antigenic heterogeneity of strains of *Saccharomyces cerevisiae* and *Candida albicans* recognized by serum antibodies from patients with Crohn's disease," *FEMS Microbiology Immunology* 89:219–224 (1992).

Pool et al., "Serum antineutrophil cytoplasmic autoantibodies in inflammatory bowel disease are mainly associated with ulcerative colitis. A correlation study between perinuclear antineutrophil cytoplasmic autoantibodies and clinical parameters, medical, and surgical treatment," *Gut* 34:46–50 (1993).

Quinton et al., "*Anti–Saccharomyces Cerevisiae* Antibodies (ASCA) Combined with Anti–Neutrophil Antibodies (ANCA) Differentiate Crohn's Disease from Ulcerative Colitis," *Gastroenterol.* 112:A1066 (1997).

Saxon et al., "A distinct subset of antineutrophil cytoplasmic antibodies is associated with inflammatory bowel disease," *J. Allergy Clin. Immunol.* 86:202–210 (1990).

Seidman et al., "Disease Specific Diagnostic Accuracy of New Serological Test in Pediatric IBD," *Gastroenterol.* 112:A1087 (1997).

Sendid et al., "Specific Antibody Response to Oligomannosidic Epitopes in Crohn's Disease," *Clinical and Diagnostic Laboratory Immunology* 3:219–226 (1996).

Vasiliauskas et al., "Stratification of Crohn's Disease by Antineutrophil Cytoplasmic Antibodies (ANCA) & Anti–*Saccharomyces* Cerevisiae Antibody (ASCA) Distinguishes Phenotypic Subgroups," *Gastroenterol.* 112:A1112 (1997).

Young et al., "Lymphocyte Proliferation Response to Baker's Yeast in Crohn's Disease," *Digestion* 55:40–43 (1994).

Colombel et al, Clinical and Experimental Immunology, 112 (Suppl. 1), 22, 1998.*

\* cited by examiner

Primary Examiner—David Sauders
(74) *Attorney, Agent, or Firm*—Campbell & Flores LLP

(57) ABSTRACT

The present invention provides a highly sensitive method of diagnosing inflammatory bowel disease (IBD) in an individual. The method includes the steps of isolating a sample from the individual; determining by non-histological means whether the sample is positive for anti-neutrophil cytoplasmic antibodies (ANCA); determining whether the sample is positive for anti-*Saccharomyces cerevisiae* immunoglobulin A (ASCA-IgA); determining whether the sample is positive for anti-*Saccharomyces cerevisiae* immunoglobulin G (ASCA-IgG); and diagnosing the individual as having IBD when the sample is positive for ANCA, ASCA-IgA or ASCA-IgG, and diagnosing the individual as not having IBD when the sample is negative for ANCA, ASCA-IgA and ASCA-IgG, provided that the method does not include histological analysis of neutrophils.

24 Claims, 1 Drawing Sheet

IBD FIRST STEP
CENTRAL COMPOSITE DESIGN

| DOE EXP. | pANCA | ASCA-A | ASCA-G | 50% IBD PREVALENCE (N=851) | | | | | 15% CALCULATED PREVALENCE (N=851) | | | | | 15% IBD PREVALENCE (N=277) | | | | |
|---|---|---|---|---|---|---|---|---|---|---|---|---|---|---|---|---|---|---|
| | | | | SENS. | SPEC. | ACC. | PPV | NPV | SENS. | SPEC. | ACC. | PPV | NPV | SENS. | SPEC. | ACC. | PPV | NPV |
| 1 | 0.5 | 10.0 | 20.0 | 96.3 | 13.6 | 55.7 | 60.5 | 78.1 | 96.3 | 13.6 | 26.0 | 16.4 | 95.4 | 100.0 | 15.7 | 28.5 | 17.5 | 100.0 |
| 2 | 0.5 | 10.0 | 60.0 | 95.2 | 14.8 | 55.7 | 53.6 | 74.7 | 95.2 | 14.8 | 26.9 | 16.5 | 94.6 | 100.0 | 17.0 | 29.6 | 17.7 | 100.0 |
| 3 | 0.5 | 30.0 | 20.0 | 96.1 | 14.4 | 55.9 | 53.8 | 77.9 | 96.1 | 14.4 | 26.7 | 16.5 | 95.4 | 100.0 | 16.6 | 29.2 | 17.7 | 100.0 |
| 4 | 0.5 | 30.0 | 60.0 | 94.9 | 16.3 | 56.3 | 54.0 | 75.6 | 94.9 | 16.3 | 28.1 | 16.7 | 94.8 | 100.0 | 18.7 | 31.1 | 18.0 | 100.0 |
| 5 | 1.5 | 10.0 | 20.0 | 81.3 | 64.6 | 73.1 | 70.4 | 76.9 | 81.3 | 64.6 | 67.1 | 28.8 | 95.1 | 81.0 | 58.3 | 61.7 | 25.4 | 94.5 |
| 6 | 1.5 | 10.0 | 60.0 | 77.1 | 75.4 | 76.3 | 76.4 | 76.1 | 77.1 | 75.4 | 75.7 | 35.6 | 94.9 | 76.2 | 69.8 | 70.8 | 31.1 | 94.3 |
| 7 | 1.5 | 30.0 | 20.0 | 78.5 | 70.8 | 74.7 | 73.6 | 76.1 | 78.5 | 70.8 | 72.0 | 32.2 | 94.9 | 73.8 | 65.1 | 66.4 | 27.4 | 93.3 |
| 8 | 1.5 | 30.0 | 60.0 | 69.5 | 86.1 | 77.7 | 83.7 | 73.2 | 69.5 | 86.1 | 83.6 | 46.9 | 94.1 | 64.3 | 82.1 | 79.4 | 39.1 | 92.8 |
| 9 | 1.0 | 20.0 | 40.0 | 82.2 | 67.3 | 74.9 | 72.2 | 78.5 | 82.2 | 67.3 | 69.5 | 30.7 | 95.5 | 85.7 | 61.3 | 65.0 | 28.3 | 96.0 |
| 10 | 1.0 | 20.0 | 40.0 | 82.2 | 67.3 | 74.9 | 72.2 | 78.5 | 82.2 | 67.3 | 69.5 | 30.7 | 95.5 | 85.7 | 61.3 | 65.0 | 28.3 | 96.0 |
| 11 | 0.5 | 20.0 | 40.0 | 94.9 | 16.3 | 56.3 | 54.0 | 75.6 | 94.9 | 16.3 | 28.1 | 16.7 | 94.8 | 100.0 | 18.7 | 31.0 | 18.0 | 100.0 |
| 12 | 1.5 | 20.0 | 40.0 | 74.1 | 83.5 | 78.7 | 82.3 | 75.7 | 74.1 | 83.5 | 82.1 | 44.2 | 94.8 | 71.4 | 78.3 | 77.3 | 37.0 | 93.9 |
| 13 | 1.0 | 10.0 | 40.0 | 85.0 | 61.0 | 73.2 | 69.3 | 79.7 | 85.1 | 61.0 | 64.6 | 27.8 | 95.8 | 90.5 | 55.7 | 61.0 | 26.8 | 97.0 |
| 14 | 1.0 | 30.0 | 40.0 | 80.6 | 57.4 | 69.2 | 66.2 | 74.1 | 80.6 | 57.4 | 60.9 | 25.0 | 94.4 | 85.7 | 62.6 | 66.1 | 29.0 | 96.1 |
| 15 | 1.0 | 20.0 | 20.0 | 85.2 | 57.7 | 71.7 | 67.6 | 79.0 | 85.2 | 57.7 | 61.8 | 26.2 | 95.7 | 85.7 | 51.9 | 57.0 | 24.2 | 95.3 |
| 16 | 1.0 | 20.0 | 60.0 | 81.8 | 67.5 | 74.7 | 72.2 | 78.1 | 81.8 | 67.5 | 69.7 | 30.8 | 95.5 | 83.3 | 63.8 | 66.8 | 29.2 | 95.5 |

Figure 1

INFLAMMATORY BOWEL DISEASE FIRST STEP ASSAY SYSTEM

BACKGROUND OF THE INVENTION

Field of the Invention

The invention relates generally to the fields of inflammatory bowel disease and immunology and more specifically to serological methods for distinguishing inflammatory bowel disease from other disorders.

BACKGROUND INFORMATION

Inflammatory bowel disease (IBD), which occurs worldwide and afflicts millions of people, is the collective term used to describe two gastrointestinal disorders of unknown etiology: Crohn's disease (CD) and ulcerative colitis (UC). IBD together with irritable bowel syndrome (IBS) will affect one-half of all Americans during their lifetime, at a cost of greater than $2.6 billion dollars for IBD and greater than $8 billion dollars for IBS. A primary determinant of these high medical costs is the difficulty of diagnosing digestive diseases. The cost of IBD and IBS is compounded by lost productivity, with persons suffering from these disorders missing at least 8 more days of work annually than the national average.

Inflammatory bowel disease has many symptoms in common with irritable bowel syndrome, including abdominal pain, chronic diarrhea, weight loss and cramping, making definitive diagnosis extremely difficult. Of the 5 million people suspected of suffering from IBD in the U.S., only 1 million are diagnosed as such. The difficulty in differentially diagnosing IBD and IBS hampers early and effective treatment of these diseases. Thus, there is a need for rapid and sensitive testing methods for definitively distinguishing IBD from IBS.

Progress has been made in precisely diagnosing, in many cases, Crohn's disease and ulcerative colitis. However, current methods for diagnosing an individual as having Crohn's disease or ulcerative colitis, while highly specific, are relatively costly, requiring labor intensive immunofluorescence assays and careful analysis of cell staining patterns. Although these costly assays are easily justified for those individuals previously diagnosed with or strongly suggested to have IBD, a less expensive but highly sensitive alternative would be advantageous for first determining if an individual has inflammatory bowel disease at all. Such a highly sensitive primary screening assay would provide physicians with an inexpensive means for rapidly distinguishing individuals with IBD from those having IBS, thereby facilitating earlier and more appropriate therapeutic intervention and minimizing uncertainty for patients and their families. If desired, such a primary screening assay could be combined with a subsequent, highly specific assay for determining if an individual diagnosed with IBD has Crohn's disease or ulcerative colitis.

Unfortunately, such a highly sensitive and inexpensive primary screening assay for distinguishing IBD from other digestive diseases presenting with similar symptoms is currently not available. Thus, there is a need for a method of rapidly diagnosing inflammatory bowel disease at a very early stage of disease progression. The present invention satisfies this need and provides related advantages as well.

SUMMARY OF THE INVENTION

The present invention provides a highly sensitive method of diagnosing inflammatory bowel disease (IBD) in an individual. The method includes the steps of isolating a sample from the individual; determining by non-histological means whether the sample is positive for anti-neutrophil cytoplasmic antibodies (ANCA); determining whether the sample is positive for anti-*Saccharomyces cerevisiae* immunoglobulin A (ASCA-IgA); determining whether the sample is positive for anti-*Saccharomyces cerevisiae* immunoglobulin G (ASCA-IgG); and diagnosing the individual as having IBD when the sample is positive for ANCA, ASCA-IgA or ASCA-IgG, and diagnosing the individual as not having IBD when the sample is negative for ANCA, ASCA-IgA and ASCA-IgG, provided that the method does not include histological analysis of neutrophils. In a method of the invention, ANCA, ASCA-IgA or ASCA-IgG positivity can be conveniently determined, for example, using an immunoassay.

The present invention further provides a highly sensitive method of diagnosing IBD in an individual. This method of the invention includes the steps of isolating a sample from the individual; determining by non-histological means whether the sample has an ANCA level above an ANCA cut-off value (X); determining whether the sample has an ASCA-IgA level above an ASCA-IgA cut-off value (Y); determining whether the sample has an ASCA-IgG level above an ASCA-IgG cut-off value (Z); and diagnosing the individual as having IBD when the ANCA level is above X, the ASCA-IgA level is above Y, or the ASCA-IgG level is above Z, and diagnosing the individual as not having IBD when the ANCA level is below X, the ASCA-IgA level is below Y, and the ASCA-IgG value is below Z, where X, Y, and Z are independently selected to achieve optimized sensitivity, specificity, negative predictive value, positive predictive value or overall agreement, provided that the method does not include histological analysis of neutrophils.

In a highly sensitive method of diagnosing IBD provided by the present invention, X, Y and Z can be independently selected such that, for example, the sensitivity of diagnosing an individual with IBD is at least about 70%, and can be selected such that, additionally, the specificity of diagnosing an individual with IBD is 30–60%. In addition, X, Y and Z can be independently selected such that the sensitivity of diagnosing an individual with IBD is at least about 70%, the specificity of diagnosing an individual with IBD is 30–60%, and the negative predictive value in a population having an IBD disease prevalence of about 15% is at least about 90% and can be, for example, at least about 95%.

Furthermore, X, Y and Z can be independently selected such that the sensitivity of diagnosing an individual with IBD is at least about 90%, and can be selected such that, additionally, the specificity of diagnosing an individual with IBD is 20–60%. If desired, X, Y and Z can be independently selected such that the sensitivity of diagnosing an individual with IBD is at least about 90%, the specificity of diagnosing an individual with IBD is 20–60%, and the negative redictive value in a population having an IBD disease revalence of about 15% is at least about 90%. The negative predictive value can be, for example, at least about 95%. In addition, X, Y and Z can be independently selected such that, for example, the sensitivity of diagnosing an individual with IBD is about 90%, the specificity is about 37%, and the negative predictive value in a population having an IBD disease prevalence of about 15% is at least about 95%. In one embodiment, X can be selected to be 0.7 multiplied by two standard deviations above the background value of ANCA-negative UC sera, Y can be selected to be 12 ELISA units, and Z can be selected to be 60 ELISA units.

In a method of the invention for diagnosing inflammatory bowel disease, the ANCA, ASCA-IgA and ASCA-IgG levels can be determined using, for example, a serum sample or saliva sample. ANCA levels can be determined using an antigen specific for ANCA such as fixed neutrophils, and ASCA-IgA and ASCA-IgG levels can be determined using an antigen specific for ASCA such as yeast cell wall phosphopeptidomannan (PPM), which can be prepared, for example, from strain ATCC #38926.

The invention additionally provides a highly efficient method of analyzing multiple samples for IBD by first assaying all samples for the presence or absence of ANCA; next assaying only ANCA-negative samples for the presence or absence of ASCA-IgA; and next assaying only ANCA-negative and ASCA-IgA-negative samples for the presence or absence of ASCA-IgG, where the presence of pANCA, ASCA-IgA or ASCA-IgG in a sample is indicative of IBD and where the absence of ANCA, ASCA-IgA and ASCA-IgG is indicative of the absence of IBD. In such a method of the invention, the presence of ANCA, ASCA-IgA and ASCA-IgG can be conveniently determined, for example, using an immunoassay.

BRIEF DESCRIPTION OF THE DRAWINGS

FIG. 1 shows the IBD First Step central composite design.

DETAILED DESCRIPTION OF THE INVENTION

The present invention is directed to the discovery that three enzyme-linked immunosorbent assays (ELISAs) can be combined without immunofluorescence or other histological analysis of neutrophils to diagnose inflammatory bowel disease (IBD) with high sensitivity. In particular, as disclosed in Example II, an ELISA assay for anti-neutrophil cytoplasmic antibodies (ANCA), an ELISA assay for anti-*Saccharomyces cerevisiae* immunoglobulin A (ASCA-IgA) and an ELISA assay for anti-*Saccharomyces cerevisiae* immunoglobulin G (ASCA-IgG) were combined to produce a highly sensitive means of distinguishing individuals having either Crohn's disease (CD) or ulcerative colitis (UC) from other individuals, such as those having irritable bowel syndrome (IBS). Such a method does not include labor intensive immunofluorescence analysis of fixed neutrophils or other neutrophil histological analysis. Thus, the methods of the invention provide a rapid and sensitive means of differentiating individuals having either CD or UC from those who do not have IBD. The methods of the invention can be used alone to rule out inflammatory bowel disease in an individual suspected of having the disease, or, when positive for diagnosis of IBD, can be used in combination with a subsequent assay that specifically differentiates CD from UC.

Thus, the present invention provides a highly sensitive method of diagnosing IBD in an individual. The method includes the steps of isolating a sample from the individual; determining by non-histological means whether the sample is positive for ANCA; determining whether the sample is positive for ASCA-IgA; determining whether the sample is positive for ASCA-IgG; and diagnosing the individual as having IBD when the sample is positive for ANCA, ASCA-IgA or ASCA-IgG, and diagnosing the individual as not having IBD when the sample is negative for ANCA, ASCA-IgA and ASCA-IgG, provided that the method does not include histological analysis of neutrophils. In a method of the invention, ANCA, ASCA-IgA and ASCA-IgG positivity can be determined, for example, using an immunoassay.

As used herein, the term "inflammatory bowel disease" is synonymous with "IBD" and is a collective term referring to both Crohn's disease and ulcerative colitis. Thus, an individual having either Crohn's disease or ulcerative colitis is defined herein as having IBD. Conversely, an individual having neither ulcerative colitis nor Crohn's disease does not have IBD as defined herein. The term "inflammatory bowel disease" distinguishes Crohn's disease and ulcerative colitis from all other disorders, syndromes or abnormalities of the gastroenterological tract including irritable bowel syndrome.

The methods of the invention for diagnosing IBD involve determining whether a sample is positive for anti-neutrophil cytoplasmic antibodies (ANCA). Anti-neutrophil cytoplasmic antibodies that produce a perinuclear staining pattern (pANCA) are elevated in 60–80% of UC patients and less frequently in CD and other disorders of the colon. Serum titers of ANCA are elevated in UC patients regardless of clinical status and, thus, do not reflect disease activity. High levels of serum ANCA also persist in UC patients five years post-colectomy. Although pANCA is found only very rarely in healthy adults and children, healthy relatives of UC patients have an increased frequency of pANCA, indicating that pANCA may be an immunogenetic susceptibility marker. ANCA reactivity is also present in a small portion of patients with Crohn's disease. The reported prevalence in CD varies, with most studies reporting that 10 to 30% of CD patients express ANCA (Saxon et al., *J. Allergy Clin. Immunol.* 86:202–210 (1990); Cambridge et al., *Gut* 33:668–674 (1992); Pool et al., *Gut* 3446–50 (1993); and Brokroelofs et al., *Dig. Dis. Sci.* 39:545–549 (1994)).

As used herein, the term "anti-neutrophil cytoplasmic antibody" is synonymous with "ANCA" and means antibodies to cytoplasmic components of a neutrophil. ANCA, such as serum or saliva ANCA, can be detected using an enzyme-linked immunosorbent assay with alcohol-fixed neutrophils, for example (see Example I). As disclosed herein, ANCA activity is divided into several broad categories: perinuclear to nuclear staining or cytoplasmic staining with perinuclear highlighting (pANCA); cytoplasmic neutrophil staining without perinuclear highlighting (cANCA); and diffuse staining with speckling across the entire neutrophil (SAPPA). The term ANCA, as used herein, encompasses all varieties of anti-neutrophils cytoplasmic reactivity, including pANCA, cANCA and SAPPA. Similarly, the term "ANCA" encompasses all immunoglobulin isotypes including, for example, immunoglobulin A and G.

The determination of whether a sample is positive for ANCA using non-histological means is made using antigen specific for ANCA. Such an antigen specific for ANCA can be, for example, whole fixed neutrophils; an unpurified or partially purified neutrophil extract; a purified UC pANCA antigen such as a purified protein, protein fragment or synthetically produced peptide; an anti-ANCA idiotypic antibody; or the like. Particularly useful antigens specific for ANCA are peptides, which can be chemically synthesized or expressed on the surface of phage. Purified antigens specific for ANCA can be, for example, histone H1, or an ANCA-reactive fragment of histone H1, as described in U.S. Pat. No. 6,074,835 now U.S. Pat. No. 6,074,835; an ulcerative colitis pANCA secretory vesicle antigen or an ANCA-reactive fragment thereof, as described in U.S. application Ser. No. 08/804,106; or a microbial UC pANCA antigen, such as a histone H1-like antigen, porin antigen, Bacteroides antigen, or ANCA-reactive fragment thereof, as described in U.S. Pat. No. 6,033,864 now U.S. Pat. No. 6,033,864. One skilled in the art understands that additional antigens specific for ANCA, including antigenic fragments and ANCA-reactive peptides, can be identified, for example, using a representative UC pANCA monoclonal antibody, such as one described in U.S. application Ser. No. 08/472,688, now abandoned.

In the methods of the invention, a sample to be analyzed is obtained from the individual to be diagnosed. The term "sample," as used herein, means any biological specimen obtained from an individual that contains antibodies. A sample can be, for example, whole blood, plasma, saliva or other bodily fluid or tissue having antibodies, preferably a serum sample. Preferably, although not necessarily, a sample contains both ANCA and ASCA antibodies. The use of a serum sample is described in Example I; the use of other samples, such as saliva and urine samples, is well known in the art (see, for example, Hashida et al., *J. Clin. Lab. Anal.* 11:267–86 (1997), which is incorporated by reference herein). One skilled in the art understands that samples such as serum samples can be diluted prior to analysis of ANCA, ASCA-IgA and ASCA-IgG content.

The methods of the invention for diagnosing IBD also involve determining whether a sample is positive for immunoglobulin A anti-*Saccharomyces cerevisiae* antibodies (ASCA-IgA) or immunoglobulin G anti-*Saccharomyces cerevisiae* antibodies (ASCA-IgG). Previous reports indicate that such antibodies can be elevated in patients having Crohn's disease, although the nature of the *S. cerevisiae* antigen supporting the specific antibody response in CD is unknown (Sendid et al., *Clin. Diag. Lab. Immunol.* 3:219–226 (1996), which is incorporated herein by reference). ASCA may represent a response against yeasts present in common food or drink or a response against yeasts that colonize the gastrointestinal tract. Studies with periodate oxidation have shown that the epitopes recognized by ASCA in CD patient sera contain polysaccharides. Oligomannosidic epitopes are shared by a variety of organisms including different yeast strains and genera, filamentous fungi, viruses, bacteria and human glycoproteins. Thus, mannose-induced antibody responses in CD may represent a response against a pathogenic yeast organism or against a cross-reactive oligomannosidic epitope present, for example, on a human glycoprotein autoantigen. Regardless of the nature of the antigen, elevated levels of serum ASCA are believed to be a differential marker for Crohn's disease, with only low levels of ASCA reported in UC patients (Sendid et al., supra, 1996).

As used herein, the term "anti-*Saccharomyces cerevisiae* immunoglobulin A" is synonymous with "ASCA-IgA" and refers to antibodies of the immunoglobulin A isotype that react specifically with *S. cerevisiae*. Similarly, the term "anti-*Saccharomyces cerevisiae* immunoglobulin G" is synonymous with "ASCA-IgG" and refers to antibodies of the immunoglobulin G isotype that react specifically with *S. cerevisiae*. The determination of whether a sample is positive for ASCA-IgA or ASCA-IgG is made using an antigen specific for ASCA. Such an antigen can be any antigen or mixture of antigens that is bound specifically by immunoglobulin A ASCA or immunoglobulin G ASCA. Although ASCA antibodies were initially characterized by their ability to bind *S. cerevisiae*, those of skill in the art will understand that an antigen that is bound specifically by ASCA can be obtained from *S. cerevisiae*, or can be obtained from a variety of other sources so long as the antigen is capable of binding specifically to ASCA antibodies. Accordingly, exemplary sources of an antigen specific for ASCA, which can be used to determine whether a sample is positive for ASCA-IgA or ASCA-IgG, include whole killed yeast cells, such as Saccharomyces or Candida cells; yeast cell wall phosphopeptidomannan (PPM); oligomannosides; neoglycolipids; anti-ASCA idiotypic antibodies; and the like. As described above, different species and strains of yeast, including Saccharomyces, can be an antigen specific for ASCA useful for determining whether a sample is positive for ASCA-IgA or ASCA-IgG. For example, *S. cerevisiae* strain Su1, Su2, CBS 1315 or BM 156, or *Candida albicans* strain VW32, can be used as an antigen specific for ASCA in a method of the invention.

Preparations of yeast cell wall mannans, or phosphopeptidomannans (PPM), are can be used to determine if a sample is positive for ASCA-IgA or ASCA-IgG. Such water soluble surface antigens can be prepared by appropriate extraction techniques, including autoclaving as described in Example I, or can be obtained commercially (see Lindberg et al., *Gut* 33:909–913 (1992), which is incorporated herein by reference). The acid stable fraction of yeast cell wall PPM also can be useful in the methods of the invention (Sendid et al., supra, 1996). An exemplary PPM that is useful in determining whether a sample is positive for ASCA-IgA or ASCA-IgG is derived from *S. cerevisiae* strain ATCC #38926.

Purified oligosaccharide antigens, such as oligomannosides, also can be useful in determining whether a sample is positive for ASCA-IgA or ASCA-IgG in a method of the invention. For use herein, the purified oligomannoside antigens are preferably converted into neoglycolipids as described in Faille et al., *Eur. J. Microbiol. Infect. Dis.* 11:438–446 (1992). One skilled in the art understands that the reactivity of such an oligomannoside antigen with ASCA can be optimized by varying the mannosyl chain length (Frosh et al., *Proc Natl. Cad. Sci. USA*, 82:1194–1198 (1985)); the anomeric configuration (Fukazawa et al., In E. Kurstak (ed.), *Immunology of Fungal Disease*, Marcel Dekker Inc., New York, pp. 37–62 (1989); Nishikawa et al, *Microbiol. Immunol.*, 34:825–840 (1990); Poulain et al., *Eur. J. Clin. Microbiol*, 23:46–52 (1993); Shibata et al., *Arch. Biochem. Biophys.*, 243:338–348 (1985); and Trinel et al., *Infect. Immun.*, 60:3845–3851 (1992)); or the position of the linkage (Kikuchi et al., *Planta*, 190:525–535 (1993)). Each of the foregoing references are incorporated herein by reference in their entirety.

An antigen specific for ASCA useful in determining whether a sample is positive for ASCA-IgA or ASCA-IgG can be, for example, an oligomannoside which includes the mannotetraose Man(1→3)Man(1→2) Man(1→2)Man. Such an oligomannoside can be purified from PPM as described in Faille et al., supra, 1992. An exemplary neoglycolipid which is an antigen specific for ASCA can be constructed by releasing the oligomannoside from its respective PPM and subsequently coupling the released oligomannoside to 4-hexadecylaniline or the like.

Prior to the present invention, ANCA and ASCA analysis have been combined in order, for example, to increase the specificity of an assay for differentiating UC from Crohn's disease or to determine clinical subtypes of CD (Quinton et al., *Gastroenterol.* 112: A1066 (1997); Seidman et al., *Gastroenterol.* 112: A1087 (1997); and Vasiliauskas et al., *Gastroenterol.* 112: A1112 (1997)). In contrast, the methods of the present invention, which are of high sensitivity, are directed to determining if an individual has either UC or CD but do not distinguish between the two diseases. Thus, the methods of the invention are useful, for example, to sensitively distinguish between IBD and other digestive disorders such as irritable bowel syndrome and infectious digestive diseases and, when positive for IBD, can be used in conjunction, if desired, with a subsequent specific assay in order to precisely determine whether the individual with IBD has UC or CD. Furthermore, previous studies in which ANCA analysis has been combined with analysis of ASCA-IgA and ASCA-IgG have additionally included immunofluorescence of fixed neutrophils in order to determine the type of ANCA reactivity present (see Quinton et al., supra, 1997; Seidman et al., supra, 1997; Dubinsky et al., supra, 1997; and Vasiliauskas et al., supra, 1997). In contrast to these studies, the methods of the present invention explicitly exclude histological analysis of neutrophils.

Thus, the present invention is directed to a highly sensitive method of diagnosing inflammatory bowel disease, which does not include histological analysis of neutrophils. As used herein, the term "histological analysis of neutrophils" means any technique revealing the structure of a neutrophilic cell using staining or microscopy. Histological analysis, which encompasses techniques such as immunocytochemistry and indirect immunofluorescence, as well as other methods involving microscopy, is explicitly excluded from the present invention. In contrast, an enzyme-linked immunosorbent assay (ELISA), in which neutrophil reactivity is analyzed by means of a detectable secondary antibody that generates a quantitative signal, does not involve microscopy or other analysis of cell structure and, therefore, is not "histological analysis of neutrophils" as defined herein.

As further disclosed herein, three ELISA cut-off values for determining if a sample is positive or negative for ANCA ("X"), ASCA-IgA ("Y") and ASCA-IgG ("Z") were simultaneously varied using Factorial Design Optimization to achieve a desired degree of sensitivity (Example II). Using this approach, cooperative interactions among the ANCA, ASCA-IgA and ASCA-IgG cut-off values were identified. For example, particular ANCA, ASCA-IgA and ASCA-IgG cut-off values were determined to diagnose an individual with IBD with greater than about 90% sensitivity, which is a greater than 90% probability that an individual having IBD by colonoscopic, radiologic and/or histologic criteria would be diagnosed as such. Thus, the present invention provides a method of diagnosing inflammatory bowel disease with a greater sensitivity than previously available. Similarly, using Factorial Design Optimization, for example, other ANCA, ASCA-IgA and ASCA-IgG cut-off values can be determined which provide a clinically useful sensitivity, specificity, negative predictive value, positive predictive value or overall agreement for a particular patient population. If desired, one can select the ANCA, ASCA-IgA and ASCA-IgG cut-off values "X," "Y," and "Z" to give a desired sensitivity combined with, for example, a desired specificity and negative predictive value.

The present invention therefore provides a highly sensitive method of diagnosing IBD in an individual by isolating a sample from the individual; determining by non-histological means whether the sample has an ANCA level above an ANCA cut-off value (X); determining whether the sample has an ASCA-IgA level above an ASCA-IgA cut-off value (Y); determining whether the sample has an ASCA-IgG level above an ASCA-IgG cut-off value (Z); and diagnosing the individual as having IBD when the ANCA level is above X, the ASCA-IgA level is above Y, or the ASCA-IgG level is above Z, and diagnosing the individual as not having IBD when the ANCA level is below X, the ASCA-IgA level is below Y, and the ASCA-IgG value is below Z, where X, Y, and Z are independently selected to achieve an optimized sensitivity, specificity, negative predictive value, positive predictive value or overall agreement, provided that the method does not include histological analysis of neutrophils.

As used herein, the term "X" refers to an ANCA cut-off value, against which an experimental ANCA sample value is compared. Similarly, as used herein, the term "Y" refers to an ASCA-IgA cut-off value, against which an experimental ASCA-IgA value is compared. The term "Z," as used herein, refers to an ASCA-IgG cut-off value, against which an experimental ASCA-IgG cut-off value is compared. As disclosed herein, when an ANCA level is above X, or an ASCA-IgA level is above Y, or an ASCA-IgG level is above Z, an individual is diagnosed as having IBD.

The clinical parameters of sensitivity, specificity, negative predictive value, positive predictive value and overall agreement are calculated using true positives, false positives, false negatives and true negatives. A "true positive" sample is a sample positive for IBD according to colonoscopic, radiologic and/or histologic analysis, which is also diagnosed positive according to a method of the invention. A "false positive" sample is a sample negative for IBD by colbnoscopic, radiologic and/or histologic analysis, which is diagnosed positive according to a method of the invention. Similarly, a "false negative" is a sample positive for IBD by colonoscopic, radiologic and/or histologic analysis, which is diagnosed negative according to a method of the invention. A "true negative" is a sample negative for IBD by colonoscopic, radiologic and/or histologic analysis, and also negative for IBD according to a method of the invention. See, for example, Motulsky (Ed.), *Intuitive Biostatistics* New York: Oxford University Press (1995), which is incorporated herein by reference.

As used herein, the term "sensitivity" means the probability that a laboratory method is positive in the presence of IBD. Sensitivity is calculated as the number of true positive results divided by the sum of the true positives and false negatives. Sensitivity essentially is a measure of how well a method correctly identifies those with disease. In a method of the invention, the ANCA, ASCA-IgA, and ASCA-IgG values can be selected such that the sensitivity of diagnosing an individual is at least about 60%, and can be, for example, at least about 65%, 70%, 75%, 80%, 85%, 90% or 95%. As illustrated in Example II, the maximum sensitivity of diagnosing IBD using a method of the invention is about 96.5%. A method of diagnosing IBD in an individual is particularly useful when the sensitivity is at least about 80%, or at least about 90%.

As used herein, the term "specificity" means the probability that a method is negative in the absence of IBD. Specificity is calculated as the number of true negative results divided by the sum of the true negatives and false positives. Specificity essentially is a measure of how well a method excludes those who do not have IBD. In a method of the invention, the ANCA, ASCA-IgA, and ASCA-IgG cut-off values "X," "Y," and "Z" can be selected such that, when the sensitivity is at least about 70%, the specificity of diagnosing an individual is in the range of 30–60%, for example, 35–60%, 40–60%, 45–60% or 50–60%. Furthermore, in a method of the invention, the ANCA, ASCA-IgA, and ASCA-IgG cut-off values "X," "Y," and "Z" can be selected such that, when the sensitivity is at least about 90%, the specificity of diagnosing an individual is in the range of 20–60%, for example, 20–30%, 20–40%, 20–50%, 30–60%, 35–60%, 40–60%, 45–60% or 50–60%. As illustrated in Example II, the maximum specificity that can be obtained in diagnosing IBD using a method of the invention is about 87.5%.

In a further embodiment, the ANCA, ASCA-IgA, and ASCA-IgG cut-off values "X," "Y," and "Z" can be independently selected, for example, such that the negative predictive value in a patient population having an IBD disease prevalence of about 15% is at least about 95%.

The term "negative predictive value," as used herein, is synonymous with "NPV" and means the probability that an individual diagnosed as not having IBD actually does not have the disease. Negative predictive value can be calculated as the number of true negatives divided by the sum of the true negatives and false negatives. Negative predictive value is determined by the characteristics of the diagnostic method as well as the prevalence of the disease in the population analyzed. In a method of the invention, the ANCA, ASCA-IgA, and ASCA-IgG cut-off values can be selected such that the negative predictive value in a population having an IBD disease prevalence is in the range of 80–99% and can be, for example, at least about 85%, at least about 90%, or at least about 95%. In particular, in a population having an IBD disease prevalence of 1 to 2%, the negative predictive value can be, for example, at least about 85%, 90%, 95%, 96%, 97%, 98% or 99%.

Predictive values, including negative and positive predictive values, are influenced by the prevalence of the disease in the population analyzed. In the methods of the invention, the cut-off values X, Y and Z can be selected to produce a desired clinical parameter for a clinical population with a particular IBD disease prevalence. For example, cut-off values X, Y and Z can be selected for an IBD disease prevalence of about 10%, 12%, 15%, 18% or 20%, which can be seen, for example, in a gastroenterologist's office. Cut-off values X, Y, and Z also can be selected for an IBD disease prevalence of about 1%, 2%, 3%, 4%, 5%, 6%, 7% or 8%. An IBD disease prevalence of 1 to 2% is typical of the disease prevalence seen in a general doctor's office.

In a method of the invention, the ANCA, ASCA-IgA, and ASCA-IgG cut-off values "X," "Y," and "Z" can be selected such that, when the sensitivity of diagnosing an individual with IBD is at least about 70% and the specificity of diagnosing an individual with IBD is in the range of 30–60%, the negative predictive value in a population having an IBD disease prevalence of about is at least about 90%. X, Y and Z can be selected such that, for example, the sensitivity is at least about 70%, the specificity is 30–60%, and the negative predictive value in a population having an IBD disease prevalence of about 15% is greater than 95%. Furthermore, in a method of the invention, the ANCA, ASCA-IgA, and ASCA-IgG cut-off values "X," "Y," and "Z" can be selected such that, when the sensitivity of diagnosing an individual with IBD is at least about 90% and the specificity of diagnosing an individual with IBD is in the range of 20–60%, the negative predictive value in a population having an IBD disease prevalence of about 15% is at least about 90%, for example, at least about 95%.

In a method of the invention, the ANCA, ASCA-IgA, and ASCA-IgG cut-off values "X," "Y," and "Z" can be selected such that, when the sensitivity of diagnosing an individual with IBD is at least about 70% and the specificity of diagnosing an individual with IBD is in the range of 20–60%, the negative predictive value in a population having an IBD disease prevalence of about 1–2% is at least about 98%. The values X, Y and Z can be selected such that the sensitivity is at least about 90%, the specificity of diagnosing an individual with IBD is 20–60%, and the negative predictive value in a population having an IBD disease prevalence of about 1–2% is greater than 98%. The negative predictive value in such a population can be, for example, greater than 99%.

In another embodiment, the ANCA, ASCA-IgA, and ASCA-IgG cut-off values "X," "Y," and "Z" can be independently selected such that, for example, the positive predictive value in a patient population having an IBD disease prevalence of about 15% is at least about 5%.

The term "positive predictive value," as used herein, is synonymous with "PPV" and means the probability that an individual diagnosed as having IBD actually has the disease. Positive predictive value can be calculated as the number of true positives divided by the sum of the true positives and false positives. Positive predictive value is determined by the characteristics of the diagnostic method as well as the prevalence of the disease in the population analyzed. In a method of the invention, the ANCA, ASCA-IgA, and ASCA-IgG cut-off values can be selected such that the positive predictive value of the method in a population having an IBD disease prevalence of 15% is at least about 5%, and can be, for example, at least about 8%, 10%, 15%, 20%, 25%, 30% or 40%.

In a further embodiment of the invention, the ANCA, ASCA-IgA, and ASCA-IgG cut-off values "X," "Y," and "Z" can be independently selected such that, for example, overall agreement in a patient population having an IBD disease prevalence of about 15% is at least about 45%.

As used herein, the term "overall agreement" means the accuracy with which a method diagnoses a disease state. Overall agreement is calculated as the sum of the true positives and true negatives divided by the total number of sample results and is affected by the prevalence of IBD in the population analyzed. The ANCA, ASCA-IgA, and ASCA-IgG cut-off values can be selected such that the overall agreement of a method of the invention in a patient population having an IBD disease prevalence of 15% is at least about 45%, and can be, for example, at least about 50%, 55% or 60%.

One skilled in the art can select an ANCA cut-off "X," an ASCA-IgA cut-off "Y," and an ASCA-IgG cut-off "Z" to achieve one or more clinically useful parameters, such as a desired sensitivity or specificity, or a desired negative predictive value, positive predictive value or overall agreement for a patient population having a particular disease prevalence. Factorial Design Optimization or Design of Experiments methodology can be used, for example, to select an appropriate ANCA cut-off "X," an ASCA-IgA cut-off "Y," and an ASCA-IgG cut-off "Z." As disclosed herein in Example II, optimization software (DOE Keep It Simple Statistically from Air Academy Associates (Colorado Springs, Colo.) was used in a central composite design experiment to simultaneously vary the three ELISA cut-offs "X," "Y," and "Z." In particular, the base ANCA cut-off was varied from 0.5 to 1.5 times the base value of approximately 10 to 20 EU; the base ASCA-IgA cut-off was varied from 10 EU to 30 EU; and the base ASCA-IgG cut-off was varied from 20 EU to 60 EU. By comparing the test results determined for the 851 individuals in the database (see Table 1) with the assigned "X," "Y," and "Z" cut-offs, each of the 851 samples were determined to be a true positive, true negative, false positive or false negative, and the clinical parameters of sensitivity, specificity, negative predictive value, positive predictive value and overall agreement were determined. Using these results, an optimized set of ANCA, ASCA-IgA and ASCA-IgG cut-off values were determined for each clinical parameter. Although the determination of the ANCA, ASCA-IgA and ASCA-IgG cut-off values "X," "Y," and "Z" is illustrated herein using the DOE KISS program, one skilled in the art understands that other computer programs for identifying cooperative interactions among multiple variables and for performing simultaneous equation calculations also can be used. For example, ECHIP optimization software, available from ECHIP, Incorporated (Hockessin, Del.), or Statgraphics optimization software, available from STSC, Incorporated (Rockville, Md.), also can be useful in determining the ANCA, ASCA-IgA and ASCA-IgG cut-off values in a method of the invention.

A variety of assay formats can be used to determine ANCA, ASCA-IgA and ASCA-IgG levels in a sample. As described above, the methods of the present invention can be performed with whole cells, such as neutrophils for the determination of ANCA levels, or yeast for the determination of ASCA-IgA or ASCA-IgG levels; with unpurified or partially purified cell extracts; or with purified proteins, protein fragments or peptides, which can be produced, for example, recombinantly, synthetically or using phage display technology.

Flow cytometry can be used to determine ANCA, ASCA-IgA and ASCA-IgG levels according to a method of the invention. Such flow cytometric assays, including bead based immunoassays, can be used to determine ANCA, ASCA-IgA and ASCA-IgG levels in the same manner as used to detect serum antibodies to Candida albicans and serum antibodies to HIV proteins (see, for example, Bishop and Davis, J. Immunol. Methods 210:79–87 (1997); McHugh et al., J. Immunol. Methods 116:213 (1989); Scillian et al., Blood 73:2041 (1989), each of which is incorporated by reference herein).

Phage display technology for expressing a recombinant antigen specific for ANCA or ASCA also can be used to determine the level of ANCA, ASCA-IgA or ASCA-IgG. Phage particles expressing the antigen specific for ANCA, or an antigen specific for ASCA, can be anchored, if desired, to a multiwell plate using an antibody such as an antiphage monoclonal antibody (Felici et al., "Phage-Displayed Peptides as Tools for Characterization of Human Sera" in Abelson (Ed.), Methods in Enzymol. 267, San Diego: Academic Press, Inc. (1996), which is incorporated by reference herein).

A variety of immunoassay formats including competitive and non-competitive immunoassay formats also are useful the methods of the invention (Self and Cook, Curr. Opin. Biotechnol. 7:60–65 (1996), which is incorporated by reference). Immunoassays encompass capillary electrophoresis based immunoassays (CEIA) and can be automated, if desired. Immunoassays also can be used in conjunction with laser induced fluorescence (see, for example, Schmalzing and Nashabeh, Electrophoresis 18:2184–93 (1997)); Bao, J. Chromatogr. B. Biomed. Sci. 699:463–80 (1997), each of which is incorporated herein by reference). Liposome immunoassays, such as flow-injection liposome immunoassays and liposome immunosensors, also can be used to determine ANCA, ASCA-IgA and ASCA-IgG levels according to a method of the invention (Rongen et al., J. Immunol. Methods 204:105–133 (1997), which is incorporated by reference herein).

Immunoassays, such as enzyme-linked immunosorbent assays (ELISAs), can be particularly useful in a method of the invention. A fixed neutrophil ELISA, for example, can be useful for determining whether a sample is positive for ANCA or for determining the ANCA level in a sample (see Example I). Similarly, an ELISA using yeast cell wall phosphopeptidomannan can be useful for determining whether a sample is positive for ASCA-IgA or ASCA-IgG, or for determining the ASCA-IgA or ASCA-IgG levels in a sample. An enzyme such as horseradish peroxidase (HRP), alkaline phosphatase (AP), β-galactosidase or urease can be linked to a secondary antibody selective for ANCA, or to a secondary antibody selective for ASCA for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm, or a urease detection system can be used with a substrate such as urea-bromocresol purple (Sigma Immunochemicals, St. Louis, Mo.). A useful secondary antibody linked to an enzyme can be obtained from a number of commercial sources; goat F(ab')$_2$ anti-human IgG-alkaline phosphatase, for example, can be purchased from Jackson Immuno-Research (West Grove, Pa.).

A radioimmunoassay also can be useful for determining whether a sample is positive for ANCA, ASCA-IgA or ASCA-IgG, or for determining the level of ANCA, ASCA-IgA or ASCA-IgG in a sample. A radioimmunoassay using, for example, an iodine-125 labeled secondary antibody (Harlow and Lane, Antibodies A Laboratory Manual Cold Spring Harbor Laboratory: New York, 1988, which is incorporated herein by reference) is encompassed within the invention.

A secondary antibody labeled with a chemiluminescent marker also can be useful in the methods of the invention. Such a chemiluminescent secondary antibody is convenient for sensitive, non-radioactive detection of ANCA, ASCA-IgA or ASCA-IgG and can be obtained commercially from various sources such as Amersham Lifesciences, Inc. (Arlington Heights, Ill.).

In addition, a detectable reagent labeled with a fluorochrome can be useful in the methods of the invention for determining whether ANCA, ASCA-IgA or ASCA-IgG is present in a sample. Appropriate fluorochromes include, for example, DAPI, fluorescein, Hoechst. 33258, R-phycocyanin, B-phycoerythrin, R-phycoerythrin, rhodamine, Texas red or lissamine. A particularly useful fluorochrome is fluorescein or rhodamine. Secondary antibodies linked to fluorochromes can be obtained commercially. For example, goat F(ab')$_2$ anti-human IgG-FITC is available from Tago Immunologicals (Burlingame, Calif.).

A signal from the detectable reagent can be analyzed, for example, using a spectrophotometer to detect color from a chromogenic substrate; a radiation counter to detect radiation, such as a gamma counter for detection of iodine-125; or a fluorometer to detect fluorescence in the presence of light of a certain wavelength. For detection of enzyme-linked reagents, a quantitative analysis of the amount of ANCA, ASCA-IgA or ASCA-IgG can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

Immunoassays using a secondary antibody selective for ANCA, or selective for ASCA-IgA, or selective for ASCA-IgG, are particularly useful in the methods of the invention. As used herein, the term "antibody" means a population of immunoglobulin molecules, which can be polyclonal or monoclonal and of any isotype. As used herein, the term "antibody" encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

The invention additionally provides a highly efficient method of analyzing multiple samples for IBD by first assaying all samples for the presence or absence of ANCA; next assaying only ANCA-negative samples for the presence or absence of ASCA-IgA; and next assaying only ANCA-negative and ASCA-IgA-negative samples for the presence or absence of ASCA-IgG, where the presence of pANCA, ASCA-IgA or ASCA-IgG in a sample is indicative of IBD and where the absence of ANCA, ASCA-IgA and ASCA-IgG is indicative of the absence of IBD. In such a method of the invention, the presence of ANCA, ASCA-IgA and ASCA-IgG can be conveniently determined, for example, using an immunoassay.

The following examples are intended to illustrate but not limit the present invention.

EXAMPLE I

Determination of Patient ANCA Status

This example describes anlysis of patient ANCA, ASCA-IgA and ASCA-IgG levels using ELISA assays.

A. Fixed Neutrophil ELISA for Determining ANCA Levels

A fixed neutrophil enzyme-linked immunosorbent assay was used to detect ANCA as described in Saxon et al., supra, 1990. Briefly, microtiter plates were coated with $2.5 \times 10^5$ neutrophils per well from peripheral human blood purified by Ficoll-hypaque centrifugation and treated with 100% methanol for 10 minutes to fix the cells. Cells were incubated with 0.25% bovine serum albumin (BSA) in phosphate-buffered saline to block nonspecific antibody binding for 60 minutes at room temperature in a humidified chamber. Next, control and coded sera were added at a 1:100 dilution to the bovine serum/phosphate-buffered saline blocking buffer and incubated for 60 minutes at room temperature in a humidified chamber. Alkaline phosphatase-conjugated goat F(ab')$_2$ anti-human immunoglobulin G antibody (γ-chain specific; Jackson Immunoresearch Labs, Inc., West Grove, Pa.) was added at a 1:1000 dilution to label neutrophil-bound antibody and incubated for 60 minutes at room temperature. A solution of p-nitrophenol phosphate substrate was added, and color development was allowed to proceed until absorbance at 405 nm in the positive control wells was 0.8–1.0 optical density units greater than the absorbance in blank wells.

A panel of twenty verified negative control samples was used with a calibrator with a defined ELISA Unit (EU) value. The base positive/negative cut-off for each ELISA run was defined as the optical density (OD) of the Calibrator minus the mean (OD) value for the panel of twenty negatives (plus 2 standard deviations) times the EU value of the Calibrator. The base cut-off value for ANCA reactivity was therefore about 10 to 20 EU, with any patient sample having an average EU value greater than the base cut-off marked as ELISA positive for ANCA reactivity. Similarly, a patient sample having an average EU value is less than or equal to the base cut-off is determined to be negative for ANCA reactivity.

B. Preparation of Yeast Cell Wall Mannan for ASCA ELISA Assay

Yeast cell wall mannan was prepared as follows and as described in Faille et al., *Eur. J. Clin. Microbiol. Infect. Dis.* 11:438–446 (1992) and in Kocourek and Ballou et al., *J. Bacteriol* 100:1175–1181 (1969), each of which is incorporated herein by reference. A lyophilized pellet of yeast *Saccharomyces uvarum* was obtained from the American Type Culture Collection (#38926). Yeast were reconstituted in 10 ml 2× YT medium, prepared according to Sambrook et al., *Molecular Cloning* Cold Spring Harbor Laboratory Press (1989), which is incorporated herein by reference. *S. uvarum* were grown for two to three days at 30° C. The terminal *S. uvarum* culture was inoculated on a 2× YT agar plate and subsequently grown for two to three days at 30° C. A single colony was used to inoculate 500 ml 2× YT media, and grown for two to three days at 30° C. Fermentation media (pH 4.5) was prepared by adding 20 gm glucose, 2 gm bacto-yeast extract, 0.25 gm MgSO$_4$ and 2.0 ml 28% H$_3$PO$_4$ per liter distilled water. The 500 ml culture was used to inoculate 50 liters of fermentation media, and the culture fermented for three to four days at 37° C.

*S. uvarum* mannan extract was prepared by adding 50 ml 0.02 M citrate buffer (5.88 gm/l sodium citrate; pH 7.0+/−0.1) to each 100 grams of cell paste. The cell/citrate mixture was autoclaved at 125° C. for ninety minutes and allowed to cool. After centrifuging at 5000 rpm for 10 minutes, the supernatant was removed and retained. The cells were then washed with 75 ml 0.02 M citrate buffer and the cell/citrate mixture again autoclaved at 125° C. for ninety minutes. The cell/citrate mixture was centrifuged at 5000 rpm for 10 minutes, and the supernatant retained.

In order to precipitate copper/mannan complexes, an equal volume of Fehling's Solution was added to the combined supernatants while stirring. The complete Fehling's solution was prepared by mixing Fehling's Solution A with Fehling's Solution B in a 1:1 ratio just prior to use. The copper complexes were allowed to settle, and the liquid decanted gently from the precipitate. The copper/mannan precipitate complexes were then dissolved in 6–8 ml 3N HCl per 100 grams yeast paste.

The resulting solution was poured with vigorous stirring into 100 ml of 8:1 methanol:acetic acid, and the precipitate allowed to settle for several hours. The supernatant was decanted and discarded; then the wash procedure was repeated until the supernatant was colorless, approximately two to three times. The precipitate was collected on a scintered glass funnel, washed with methanol and air dried overnight. On some occasions, the precipitate was collected by centrifugation at 5000 rpm for 10 minutes before washing with methanol and air drying overnight. The dried mannan ;powder was dissolved in distilled water, to a concentration of approximately 2 g/ml.

C. Preparation of *S. uvarum* Mannan ELISA Plates *S. uvarum* cell mannan ELISA plates were saturated with antigen as follows. Purified *S. uvarum* mannan prepared as described above was diluted to a concentration of 100 μg/ml with phosphate buffered saline/0.2% sodium azide (PBS-N3). Using a multi-channel pipettor, 100 μl of 100 μg/ml *S. uvarum* mannan was added per well of a Costar 96-well hi-binding plate (catalogue number 3590; Costar Corp., Cambridge, Mass.). The antigen was allowed to coat the plate at 4° C. for a minimum of 12 hours. Each lot of plates was compared to a previous lot before use. Plates were stored at 2–8° C. for up to one month.

D. ASCA ELISA Analysis of Patient Sera

Patient sera were analyzed in duplicate for anti-IgG or anti-IgA reactivity. Microtiter plates saturated with antigen as described above were incubated with-phosphate buffered saline/0.05% Tween-20 for 45 minutes at room temperature to inhibit nonspecific antibody binding. Patient sera were subsequently added at a dilution of 1:80 for ASCA-IgA and 1:800 for analysis of ASCA-IgG and incubated for 1 hour at room temperature. Wells were washed three times with PBS/0.05% Tween-20. Then a 1:1000 dilution of alkaline phosphatase-conjugated goat anti-human IgA (Jackson Immunoresearch, West Grove, Pa.) or a 1:1000 dilution of alkaline phosphatase-conjugated goat anti-human IgG F(ab')$_2$ (Pierce, Rockford, Ill.) or was added, and the microtiter plates incubated for 1 hour at room temperature. A solution of p-nitrophenol phosphate in diethanolamine substrate buffer was added, and color development allowed to proceed for 10 minutes. Absorbance at 405 nm was analyzed using an automated EMAX plate reader (Molecular Devices, Sunnyvale, Calif.).

To determine the base cut-off value for ASCA-IgA and ASCA-IgG, single point calibrators having fixed EU values were used. OD values for patients samples were compared to the OD value for the Calibrators and multiplied by the Calibrator assigned values. The base cut-off value for the ASCA-IgA ELISA was 20 EU. The base cut-off value for the ASCA-IgG was 40 EU.

EXAMPLE II

Determination of Optimized Cut-Offs for ANCA, ASCA-IgA and ASCA-IgG Positivity This example demonstrates that particular ANCA, ASCA-IgA and ASCA-IgG cut-off values can be selected to yield a preferred clinical parameter for diagnosing IBD.

A. Database Used in Analysis

Only quantitative ELISA procedures were performed and particular cut-off values for the results of each ELISA assay used to determine whether the test serum sample was positive or negative for markers of IBD. In particular, no immunofluorescence assay procedures were performed as part of these diagnostics.

The cut-off values for each of the three ELISA components of the assay were determined using a database consisting of serology data from 851 individuals (Table 1). The presence or absence of inflammatory bowel disease was made for all IBD patients by colonoscopic, radiologic, and/or histologic methods at Cedars Sinai Medical Center (Los Angeles, Calif.). Serum from 300 asymptomatic non-disease controls also was tested, although, for ethical reasons, colonoscopy was not performed on these individuals.

TABLE 1

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 1 | 1 | NON IBD | NON IBD | 8.624 | 13.374 | 5.356 | 15.516 |
| 2 | 2 | NON IBD | NON IBD | 6.606 | 13.374 | 1.379 | 10.28 |
| 3 | 3 | NON IBD | NON IBD | 6.056 | 13.374 | 3.995 | 5.874 |
| 4 | 4 | NON IBD | NON IBD | 9.602 | 13.374 | 1.697 | 12.77 |
| 5 | 5 | NON IBD | NON IBD | 6.85 | 13.374 | 1.626 | 6.449 |
| 6 | 6 | NON IBD | NON IBD | 7.462 | 13.374 | 1.997 | 12.898 |
| 7 | 7 | NON IBD | NON IBD | 7.278 | 13.374 | 2.669 | 8.684 |
| 8 | 8 | NON IBD | NON IBD | 15.229 | 13.374 | 2.881 | 11.429 |
| 9 | 9 | NON IBD | NON IBD | 11.743 | 13.374 | 1.591 | 17.431 |
| 10 | 10 | NON IBD | NON IBD | 13.7 | 13.374 | 0.389 | 4.533 |
| 11 | 11 | NON IBD | NON IBD | 12.783 | 13.374 | 2.492 | 23.434 |
| 12 | 12 | NON IBD | NON IBD | 11.07 | 13.374 | 3.853 | 6.96 |
| 13 | 13 | NON IBD | NON IBD | 9.297 | 13.374 | 11.754 | 10.599 |
| 14 | 14 | NON IBD | NON IBD | 7.951 | 13.374 | 0.548 | 4.533 |
| 15 | 15 | NON IBD | NON IBD | 9.833 | 11.989 | 0.716 | 6.065 |
| 16 | 16 | NON IBD | NON IBD | 8.135 | 13.374 | 0.813 | 5.938 |
| 17 | 17 | NON IBD | NON IBD | 7.829 | 13.374 | 12.39 | 7.471 |
| 18 | 18 | NON IBD | NON IBD | 11.988 | 13.374 | 2.863 | 26.371 |
| 19 | 19 | NON IBD | NON IBD | 5.015 | 13.374 | 1.891 | 5.938 |
| 20 | 20 | NON IBD | NON IBD | 9.358 | 13.374 | 1.98 | 4.278 |
| 21 | 21 | NON IBD | NON IBD | 8.073 | 13.374 | 1.573 | 5.747 |
| 22 | 22 | NON IBD | NON IBD | 9.419 | 13.374 | 2.492 | 11.94 |
| 23 | 23 | NON IBD | NON IBD | 5.015 | 13.374 | 1.962 | 6.641 |
| 24 | 24 | NON IBD | NON IBD | 7.278 | 13.374 | 1.502 | 13.537 |
| 25 | 25 | NON IBD | NON IBD | 9.419 | 13.374 | 3.252 | 8.875 |
| 26 | 26 | NON IBD | NON IBD | 9.174 | 13.374 | 0.442 | 4.883 |
| 27 | 27 | NON IBD | NON IBD | 19.388 | 13.374 | 5.285 | 7.854 |
| 28 | 28 | NON IBD | NON IBD | 12.355 | 13.374 | 2.563 | 5.108 |
| 29 | 29 | NON IBD | NON IBD | 6.544 | 13.374 | 5.638 | 5.172 |
| 30 | 30 | NON IBD | NON IBD | 7.278 | 13.374 | 13.504 | 15.58 |
| 31 | 31 | NON IBD | NON IBD | 7.645 | 13.374 | 4.277 | 27.137 |
| 32 | 32 | NON IBD | NON IBD | 8.624 | 13.374 | 2.722 | 4.661 |
| 33 | 33 | NON IBD | NON IBD | 20.183 | 13.374 | 3.411 | 6.002 |
| 34 | 34 | NON IBD | NON IBD | 14.434 | 13.374 | 15.006 | 19.794 |
| 35 | 35 | NON IBD | NON IBD | 16.566 | 20.956 | 6.345 | 12.643 |
| 36 | 36 | NON IBD | NON IBD | 17.9 | 20.956 | 13.398 | 17.559 |
| 37 | 37 | NON IBD | NON IBD | 10.801 | 20.956 | 2.474 | 5.683 |
| 38 | 38 | NON IBD | NON IBD | 23.726 | 20.956 | 22.642 | 37.034 |
| 39 | 39 | NON IBD | NON IBD | 16.323 | 20.956 | 1.803 | 18.198 |
| 40 | 40 | NON IBD | NON IBD | 19.114 | 20.956 | 4.313 | 11.429 |
| 41 | 41 | NON IBD | NON IBD | 22.33 | 20.956 | 3.888 | 5.108 |
| 42 | 42 | NON IBD | NON IBD | 6.371 | 20.956 | 2.404 | 2.554 |
| 43 | 43 | NON IBD | NON IBD | 17.597 | 20.956 | 13.804 | 19.475 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 44 | 44 | NON IBD | NON IBD | 14.745 | 20.956 | 1.326 | 2.937 |
| 45 | 45 | NON IBD | NON IBD | 7.16 | 20.956 | 1.827 | 4.373 |
| 46 | 46 | NON IBD | NON IBD | 13.896 | 20.956 | 1.292 | 2.345 |
| 47 | 47 | NON IBD | NON IBD | 7.585 | 20.956 | 1.846 | 6.782 |
| 48 | 48 | NON IBD | NON IBD | 10.437 | 20.956 | 0.941 | 5.134 |
| 49 | 49 | NON IBD | NON IBD | 7.282 | 20.956 | 1.034 | 21.296 |
| 50 | 50 | NON IBD | NON IBD | 13.774 | 20.956 | 1.569 | 7.606 |
| 51 | 51 | NON IBD | NON IBD | 17.718 | 20.956 | 2.215 | 6.021 |
| 52 | 52 | NON IBD | NON IBD | 11.408 | 20.956 | 0.646 | 2.535 |
| 53 | 53 | NON IBD | NON IBD | 7.949 | 20.956 | 2.363 | 9.571 |
| 54 | 54 | NON IBD | NON IBD | 14.684 | 20.956 | 1.218 | 5.704 |
| 55 | 55 | NON IBD | NON IBD | 14.867 | 20.956 | 3.784 | 7.986 |
| 56 | 56 | NON 1Bb | NON IBD | 11.529 | 20.956 | 1.2 | 10.775 |
| 57 | 57 | NON IBD | NON IBD | 21.177 | 20.956 | 2.196 | 8.43 |
| 58 | 58 | NON IBD | NON IBD | 9.527 | 20.956 | 2.639 | 9.697 |
| 59 | 59 | NON IBD | NON IBD | 12.985 | 20.956 | 2.16 | 5.894 |
| 60 | 60 | NON IBD | NON IBD | 11.59 | 20.956 | 2.436 | 22.881 |
| 61 | 61 | NON IBD | NON IBD | 10.255 | 20.956 | 0.554 | 2.028 |
| 62 | 62 | NON IBD | NON IBD | 13.592 | 20.956 | 1.218 | 5.958 |
| 63 | 63 | NON IBD | NON IBD | 13.532 | 20.956 | 1.347 | 15.211 |
| 64 | 64 | NON IBD | NON IBD | 12.500 | 20.956 | 11.228 | 98.739 |
| 65 | 65 | NON IBD | NON IBD | 12.925 | 20.956 | 2.170 | 12.131 |
| 66 | 66 | NON IBD | NON IBD | 12.318 | 20.956 | 3.780 | 12.907 |
| 67 | 67 | NON IBD | NON IBD | 16.262 | 20.956 | 7.717 | 18.478 |
| 68 | 68 | NON IBD | NON IBD | 8.897 | 21.656 | 1.767 | 3.667 |
| 69 | 69 | NON IBD | NON IBD | 7.374 | 21.656 | 1.767 | 6.7 |
| 70 | 70 | NON IBD | NON IBD | 17.550 | 21.656 | 0.895 | 33.501 |
| 71 | 71 | NON IBD | NON IBD | 20.963 | 21.656 | 6.554 | 14.247 |
| 72 | 72 | NON IBD | NON IBD | 36.868 | 21.656 | 2.774 | 7.264 |
| 73 | 73 | NON IBD | NON IBD | 15.113 | 21.656 | 1.566 | 12.342 |
| 74 | 74 | NON IBD | NON IBD | 12.371 | 21.656 | 12.749 | 9.521 |
| 75 | 75 | NON IBD | NON IBD | 13.163 | 21.656 | 2.505 | 4.373 |
| 76 | 76 | NON IBD | NON IBD | 20.353 | 21.656 | 2.505 | 8.745 |
| 77 | 77 | NON IBD | NON IBD | 28.032 | 21.656 | 4.317 | 28.211 |
| 78 | 78 | NON IBD | NON IBD | 14.869 | 21.656 | 1.253 | 4.866 |
| 79 | 79 | NON IBD | NON IBD | 15.174 | 21.656 | 4.719 | 10.297 |
| 80 | 80 | NON IBD | NON IBD | 18.952 | 21.656 | 5.681 | 32.937 |
| 81 | 81 | NON IBD | NON IBD | 25.960 | 21.656 | 36.347 | 43.868 |
| 82 | 82 | NON IBD | NON IBD | 18.342 | 21.656 | 2.438 | 11.426 |
| 83 | 83 | NON IBD | NON IBD | 21.511 | 21.656 | 1.096 | 5.36 |
| 84 | 84 | NON IBD | NON IBD | 17.002 | 21.656 | 1.856 | 6.841 |
| 85 | 85 | NON IBD | NON IBD | 18.282 | 21.656 | 4.004 | 7.758 |
| 86 | 86 | NON IBD | NON IBD | 8.775 | 21.656 | 2.572 | 2.116 |
| 87 | 87 | NON IBD | NON IBD | 12.066 | 21.656 | 4.742 | 8.534 |
| 88 | 88 | NON IBD | NON IBD | 15.844 | 21.656 | 4.563 | 29.974 |
| 89 | 89 | NON IBD | NON IBD | 15.722 | 21.656 | 1.230 | 2.892 |
| 90 | 90 | NON IBD | NON IBD | 13.528 | 21.656 | 1.163 | 4.373 |
| 91 | 91 | NON IBD | NON IBD | 19.988 | 21.656 | 6.129 | 9.169 |
| 92 | 92 | NON IBD | NON IBD | 17.002 | 21.656 | 4.317 | 25.672 |
| 93 | 93 | NON IBD | NON IBD | 18.647 | 21.656 | 0.962 | 6.982 |
| 94 | 94 | NON IBD | NON IBD | 17.733 | 21.656 | 15.545 | 33.994 |
| 95 | 95 | NON IBD | NON IBD | 16.819 | 21.656 | 9.327 | 16.715 |
| 96 | 96 | NON IBD | NON IBD | 17.550 | 21.656 | 7.269 | 18.196 |
| 97 | 97 | NON IBD | NON IBD | 13.833 | 21.656 | 3.422 | 9.733 |
| 98 | 98 | NON IBD | NON IBD | 7.861 | 21.656 | 10.244 | 7.123 |
| 99 | 99 | NON IBD | NON IBD | 14.747 | 21.656 | 2.930 | 13.048 |
| 100 | 100 | NON IBD | NON IBD | 15.661 | 21.656 | 3.623 | 15.869 |
| 101 | 101 | NON IBD | NON IBD | 15.697 | 11.989 | 3.646 | 13.4 |
| 102 | 102 | NON IBD | NON IBD | 11.231 | 11.989 | 2.214 | 10.156 |
| 103 | 103 | CD | IBD | 10.311 | 17.023 | 11.264 | 14.32 |
| 104 | 104 | CD | IBD | 49.604 | 17.023 | 4.613 | 45.98 |
| 105 | 107 | CD | IBD | 12.919 | 17.023 | 130.938 | 62.82 |
| 106 | 108 | CD | IBD | 21.242 | 17.023 | 115.841 | 85.92 |
| 107 | 110 | CD | IBD | 35.031 | 17.023 | 61.667 | 57.82 |
| 108 | 111 | UC | IBD | 6.708 | 17.023 | 31.708 | 36.87 |
| 109 | 113 | UC | IBD | 16.149 | 17.023 | 18.369 | 12.54 |
| 110 | 114 | CD | IBD | 19.565 | 17.023 | 22.501 | 31.03 |
| 111 | 115 | CD | IBD | 23.168 | 17.023 | 45.229 | 33.71 |
| 112 | 116 | CD | IBD | 16.335 | 17.023 | 10.974 | 7.46 |
| 113 | 118 | UC | IBD | 24.161 | 17.023 | 20.816 | 49.51 |
| 114 | 119 | UC | IBD | 74.596 | 17.023 | 8.419 | 13.82 |
| 115 | 122 | UC | IBD | 150.215 | 17.023 | 4.178 | 7.80 |
| 116 | 126 | CD | IBD | 17.019 | 17.023 | 128.111 | 84.87 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 117 | 127 | CD | IBD | 28.509 | 17.023 | 42.546 | 40.00 |
| 118 | 134 | CD | IBD | 30.932 | 17.023 | 9.071 | 8.27 |
| 119 | 136 | UC | IBD | 51.977 | 17.023 | 67.842 | 16.81 |
| 120 | 137 | UC | IBD | 98.417 | 17.023 | 4.558 | 13.78 |
| 121 | 138 | CONTROL | NON IBD | 14.845 | 17.023 | 2.492 | 13.88 |
| 122 | 139 | CD | IBD | 9.503 | 17.023 | 5.682 | 8.57 |
| 123 | 140 | CD | IBD | 49.683 | 17.023 | 18.840 | 10.66 |
| 124 | 142 | UC | IBD | 118.275 | 17.023 | 1.912 | 4.30 |
| 125 | 143 | CD | IBD | 22.919 | 17.023 | 4.993 | 11.66 |
| 126 | 144 | CD | IBD | 18.820 | 17.023 | 55.270 | 27.43 |
| 127 | 145 | CD | IBD | 29.130 | 17.023 | 137.028 | 118.39 |
| 128 | 146 | CONTROL | NON IBD | 38.199 | 17.023 | 18.677 | 19.53 |
| 129 | 147 | UC | IBD | 58.306 | 17.023 | 2.347 | 5.71 |
| 130 | 148 | CD | IBD | 44.472 | 17.023 | 41.658 | 25.58 |
| 131 | 149 | CD | IBD | 65.189 | 17.023 | 41.260 | 14.55 |
| 132 | 157 | CD | IBD | 17.888 | 17.023 | 27.431 | 24.61 |
| 133 | 158 | CD | IBD | 54.836 | 17.023 | 61.831 | 24.91 |
| 134 | 160 | UC | IBD | 162.181 | 17.023 | 8.292 | 9.82 |
| 135 | 166 | CD | IBD | 27.578 | 17.023 | 36.964 | 22.86 |
| 136 | 168 | CD | IBD | 21.615 | 17.023 | 134.527 | 160.93 |
| 137 | 169 | UC | IBD | 88.000 | 17.023 | 9.434 | 8.15 |
| 138 | 170 | CD | IBD | 32.298 | 17.023 | 71.201 | 48.56 |
| 139 | 174 | UC | IBD | 56.072 | 17.023 | 10.720 | 15.04 |
| 140 | 175 | CD | IBD | 43.416 | 17.023 | 2.691 | 14.38 |
| 141 | 176 | NON IBD | NON IBD | 14.472 | 17.023 | 6.588 | 5.68 |
| 142 | 178 | CD | IBD | 43.054 | 17.023 | 80.807 | 64.06 |
| 143 | 201 | CD | IBD | 16.211 | 17.023 | 31.980 | 35.14 |
| 144 | 203 | CD | IBD | 18.758 | 17.023 | 73.394 | 35.85 |
| 145 | 204 | CD | IBD | 58.400 | 17.023 | 57.010 | 112.83 |
| 146 | 206 | CD | IBD | 10.870 | 17.023 | 47.386 | 34.81 |
| 147 | 207 | CD | IBD | 11.304 | 17.023 | 95.421 | 60.64 |
| 148 | 213 | CD | IBD | 34.721 | 17.023 | 39.549 | 15.55 |
| 149 | 214 | CD | IBD | 20.311 | 17.023 | 27.289 | 25.37 |
| 150 | 216 | CD | IBD | 43.272 | 17.023 | 57.880 | 33.85 |
| 151 | 218 | CD | IBD | 21.677 | 17.023 | 23.242 | 36.56 |
| 152 | 221 | NON IBD | NON IBD | 15.776 | 17.023 | 22.296 | 10.74 |
| 153 | 223 | CONTROL | NON IBD | 8.025 | 15.673 | 16.938 | 9.44 |
| 154 | 224 | CD | IBD | 14.502 | 15.673 | 27.256 | 52.74 |
| 155 | 229 | CD | IBD | 13.474 | 15.673 | 8.129 | 14.92 |
| 156 | 231 | CD | IBD | 50.254 | 15.673 | 97.014 | 69.24 |
| 157 | 234 | CD | IBD | 46.690 | 15.673 | 45.405 | 36.68 |
| 158 | 236 | UC | IBD | 32.568 | 15.673 | 7.150 | 41.93 |
| 159 | 237 | UC | IBD | 70.695 | 15.673 | 7.780 | 8.56 |
| 160 | 238 | CONTROL | NON IBD | 11.239 | 15.673 | 2.820 | 10.32 |
| 161 | 247 | UC | IBD | 24.109 | 15.673 | 25.747 | 32.92 |
| 162 | 248 | CD | IBD | 19.517 | 15.673 | 14.615 | 21.30 |
| 163 | 249 | CD | IBD | 5.740 | 15.673 | 3.368 | 5.89 |
| 164 | 253 | CD | IBD | 30.453 | 15.673 | 7.697 | 17.54 |
| 165 | 254 | UC | IBD | 70.028 | 15.673 | 4.745 | 15.50 |
| 166 | 258 | NON IBD | NON IBD | 11.904 | 15.673 | 4.197 | 10.59 |
| 167 | 260 | CD | IBD | 59.238 | 15.673 | 7.100 | 44.96 |
| 168 | 261 | NON IBD | NON IBD | 41.390 | 15.673 | 3.019 | 9.98 |
| 169 | 262 | CD | IBD | 7.855 | 15.673 | 2.273 | 11.56 |
| 170 | 265 | UC | IBD | 73.131 | 15.673 | 4.214 | 10.80 |
| 171 | 267 | CD | IBD | 20.181 | 15.673 | 72.512 | 23.45 |
| 172 | 274 | UC | IBD | 139.985 | 15.673 | 14.267 | 11.47 |
| 173 | 275 | CD | IBD | 25.921 | 15.673 | 10.186 | 11.62 |
| 174 | 276 | UC | IBD | 93.582 | 15.673 | 11.347 | 18.33 |
| 175 | 278 | CD | IBD | 94.005 | 15.673 | 86.447 | 97.21 |
| 176 | 314 | UC | IBD | 15.529 | 15.673 | 8.245 | 15.56 |
| 177 | 321 | UC | IBD | 157.281 | 15.673 | 11.032 | 16.35 |
| 178 | 325 | NON IBD | NON IBD | 13.716 | 15.673 | 10.687 | 27.15 |
| 179 | 329 | CD | IBD | 8.097 | 15.673 | 3.878 | 7.68 |
| 180 | 334 | IBS | NON IBD | 54.583 | 15.673 | 3.557 | 26.79 |
| 181 | 339 | UC | IBD | 55.589 | 15.673 | 3.846 | 9.28 |
| 182 | 352 | CD | IBD | 24.592 | 15.673 | 124.983 | 129.22 |
| 183 | 362 | UC | IBD | 17.100 | 15.673 | 1.698 | 5.49 |
| 184 | 374 | NON IBD | NON IBD | 9.305 | 15.673 | 6.885 | 13.80 |
| 185 | 376 | CD | IBD | 13.172 | 15.673 | 119.436 | 18.33 |
| 186 | 377 | NON IBD | NON IBD | 12.508 | 15.673 | 18.331 | 8.83 |
| 187 | 384 | UC | IBD | 65.257 | 15.673 | 4.529 | 6.64 |
| 188 | 403 | UC | IBD | 83.950 | 15.673 | 18.613 | 36.49 |
| 189 | 405 | UC | IBD | 89.737 | 15.673 | 13.869 | 27.63 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 190 | 406 | CONTROL | NON IBD | 19.795 | 15.673 | 5.889 | 12.40 |
| 191 | 407 | CD | IBD | 6.949 | 15.673 | 4.960 | 29.41 |
| 192 | 409 | CD | IBD | 114.898 | 15.673 | 18.547 | 26.60 |
| 193 | 413 | UC | IBD | 24.900 | 15.673 | 2.107 | 9.60 |
| 194 | 413 | UC | IBD | 24.894 | 15.673 | 1.955 | 9.6 |
| 195 | 414 | CD | IBD | 54.475 | 15.673 | 67.817 | 102.23 |
| 196 | 416 | CONTROL | NON IBD | 15.693 | 15.673 | 6.437 | 31.19 |
| 197 | 417 | UC | IBD | 133.897 | 15.673 | 4.147 | 19.22 |
| 198 | 419 | CD | IBD | 4.411 | 15.673 | 27.090 | 79.19 |
| 199 | 420 | CD | IBD | 23.021 | 15.673 | 5.410 | 32.59 |
| 200 | 421 | CD | IBD | 65.500 | 15.673 | 43.334 | 30.13 |
| 201 | 421 | CD | IBD | 65.509 | 15.673 | 23.073 | 30.13 |
| 202 | 422 | CONTROL | NON IBD | 22.425 | 15.673 | 8.714 | 29.56 |
| 203 | 423 | UC | IBD | 37.523 | 15.673 | 7.942 | 10.85 |
| 204 | 424 | CD | IBD | 18.429 | 15.673 | 33.448 | 32.74 |
| 205 | 425 | IBS | NON IBD | 6.100 | 15.673 | 0.813 | 3.35 |
| 206 | 425 | NON IBD | NON IBD | 6.103 | 15.673 | 0.625 | 3.35 |
| 207 | 426 | NON IBD | NON IBD | 14.743 | 15.673 | 4.150 | 4.90 |
| 208 | 428 | CD | IBD | 57.780 | 15.673 | 7.583 | 9.45 |
| 209 | 429 | CD | IBD | 36.469 | 15.673 | 6.894 | 9.18 |
| 210 | 434 | NON IBD | NON IBD | 16.073 | 15.673 | −1.351 | 16.11 |
| 211 | 437 | IBS | NON IBD | 16.435 | 15.673 | 5.763 | 17.40 |
| 212 | 438 | CD | IBD | 64.824 | 15.673 | 60.141 | 36.22 |
| 213 | 443 | IBS | NON IBD | 10.808 | 15.673 | −0.262 | 6.12 |
| 214 | 444 | CD | IBD | 26.326 | 15.673 | 27.134 | 42.89 |
| 215 | 449 | CONTROL | NON IBD | 28.266 | 15.673 | 16.531 | 36.49 |
| 216 | 450 | UC | IBD | 29.598 | 15.673 | 3.157 | 18.20 |
| 217 | 451 | IBS | NON IBD | 7.238 | 15.673 | −2.344 | 5.81 |
| 218 | 453 | UC/PSC | IBD | 58.404 | 15.673 | 7.555 | 12.67 |
| 219 | 455 | UC | IBD | 65.354 | 15.673 | 11.375 | 16.34 |
| 220 | 458 | CONTROL | NON IBD | 38.163 | 15.673 | 3.819 | 8.54 |
| 221 | 461 | UC | IBD | 50.694 | 15.673 | 28.292 | 14.90 |
| 222 | 464 | CD | IBD | 30.094 | 15.673 | 100.041 | 126.70 |
| 223 | 502 | CD | IBD | 6.247 | 15.673 | 8.727 | 26.30 |
| 224 | 504 | NON IBD | NON IBD | 14.080 | 15.673 | 0.345 | 16.80 |
| 225 | 505 | NON IBD | NON IBD | 9.321 | 15.673 | 5.418 | 20.21 |
| 226 | 506 | CONTROL | NON IBD | 23.451 | 15.673 | 12.643 | 36.35 |
| 227 | 509 | CD | IBD | 64.285 | 15.673 | 10.258 | 25.51 |
| 228 | 515 | CONTROL | NON IBD | 17.744 | 15.673 | 8.934 | 23.81 |
| 229 | 531 | CD | IBD | 198.079 | 15.673 | 4.829 | 20.58 |
| 230 | 534 | CONTROL | NON IBD | 30.049 | 15.673 | 12.241 | 43.53 |
| 231 | 536 | IBS | NON IBD | 67.281 | 54.120 | 14.554 | 34.46 |
| 232 | 537 | NON IBD | NON IBD | 22.607 | 24.358 | 1.988 | 21.49 |
| 233 | 538 | CD | IBD | 65.898 | 54.120 | 98.850 | 174.86 |
| 234 | 539 | CD | IBD | 14.477 | 24.358 | 3.463 | 22.89 |
| 235 | 542 | CONTROL | NON IBD | 11.057 | 15.673 | 4.234 | 30.99 |
| 236 | 543 | UC | IBD | 69.278 | 54.120 | 7.521 | 21.74 |
| 237 | 544 | CD | IBD | 15.915 | 24.358 | 27.458 | 57.35 |
| 238 | 545 | NON IBD | NON IBD | 18.245 | 24.358 | 53.402 | 90.17 |
| 239 | 547 | IBS | NON IBD | 9.817 | 24.358 | 13.080 | 34.58 |
| 240 | 551 | IBS | NON IBD | 12.643 | 24.358 | 4.220 | 36.53 |
| 241 | 552 | CD | IBD | 71.812 | 54.120 | 16.313 | 43.47 |
| 242 | 553 | CD | IBD | 30.788 | 24.358 | 11.335 | 69.35 |
| 243 | 554 | CD | IBD | 17.501 | 24.358 | 80.752 | 97.96 |
| 244 | 557 | NON IBD | NON IBD | 11.701 | 24.358 | 5.248 | 24.11 |
| 245 | 559 | UC | IBD | 90.564 | 69.938 | 5.140 | 28.25 |
| 246 | 560 | IBS | NON IBD | 17.253 | 24.358 | 5.343 | 61.37 |
| 247 | 561 | UC | IBD | 17.005 | 24.358 | 20.506 | 22.53 |
| 248 | 562 | UC | IBD | 23.688 | 20.189 | 38.929 | 26.18 |
| 249 | 563 | CD | IBD | 26.338 | 20.189 | 3.076 | 47.37 |
| 250 | 566 | CONTROL | NON IBD | 18.601 | 20.189 | 5.613 | 32.88 |
| 251 | 567 | UC | IBD | 79.012 | 69.938 | 6.154 | 11.29 |
| 252 | 569 | CD | IBD | 19.873 | 20.189 | −0.054 | 26.60 |
| 253 | 570 | UC | IBD | 111.640 | 20.189 | 14.351 | 19.49 |
| 254 | 574 | IBS | NON IBD | 20.138 | 20.189 | 2.448 | 13.77 |
| 255 | 577 | IBS | NON IBD | 13.620 | 20.189 | 0.460 | 2.68 |
| 256 | 578 | UC | IBD | 21.516 | 20.189 | 0.852 | 4.78 |
| 257 | 579 | UC | IBD | 93.827 | 69.938 | −0.257 | 5.64 |
| 258 | 580 | CD | IBD | 18.283 | 20.189 | 23.874 | 16.22 |
| 259 | 581 | CD | IBD | 18.177 | 20.189 | 61.923 | 48.26 |
| 260 | 601 | CD | IBD | 20.880 | 20.189 | 1.772 | 6.20 |
| 261 | 603 | UC | IBD | 78.571 | 69.938 | 4.153 | 6.20 |
| 262 | 604 | UC | IBD | 189.947 | 69.938 | 7.291 | 27.68 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 263 | 605 | UC | IBD | 37.149 | 20.189 | 3.896 | 9.00 |
| 264 | 608 | UC | IBD | 76.984 | 69.934 | 29.533 | 23.72 |
| 265 | 609 | UC/PSC | IBD | 60.934 | 69.934 | 22.143 | 24.90 |
| 266 | 610 | UC | IBD | 67.356 | 20.189 | 4.634 | 3.63 |
| 267 | 613 | UC | IBD | 50.026 | 20.189 | 5.018 | 22.93 |
| 268 | 616 | UC | IBD | 86.507 | 69.938 | 5.519 | 12.9 |
| 269 | 622 | UC | IBD | 50.609 | 20.189 | 9.327 | 13.93 |
| 270 | 623 | UC | IBD | 117.724 | 69.938 | 6.198 | 8.48 |
| 271 | 625 | CD | IBD | 13.937 | 20.189 | 27.597 | 39.58 |
| 272 | 627 | NON IBD | NON IBD | 13.620 | 20.189 | 2.420 | 6.24 |
| 273 | 628 | CD | IBD | 77.865 | 69.938 | 131.730 | 225.41 |
| 274 | 629 | UC/PSC | IBD | 27.663 | 20.189 | 2.656 | 4.62 |
| 275 | 631 | IBS | NON IBD | 14.467 | 20.189 | 5.224 | 10.54 |
| 276 | 632 | UC | IBD | 86.963 | 20.189 | 6.523 | 12.43 |
| 277 | 633 | NON IBD | NON IBD | 18.972 | 20.189 | 1.623 | 3.47 |
| 278 | 634 | IBS | NON IBD | 17.064 | 20.189 | 3.040 | 6.55 |
| 279 | 637 | UC | IBD | 154.637 | 20.189 | 4.162 | 3.51 |
| 280 | 639 | UC | IBD | 85.957 | 20.189 | 6.612 | 18 |
| 281 | 647 | NON IBD | NON IBD | 14.891 | 20.189 | 2.066 | 6.08 |
| 282 | 648 | UC | IBD | 63.328 | 20.189 | 4.309 | 110.18 |
| 283 | 650 | CD | IBD | 38.951 | 20.189 | 157.231 | 92.74 |
| 284 | 651 | UC | IBD | 59.088 | 20.189 | 47.816 | 34.93 |
| 285 | 660 | UC | IBD | 85.841 | 16.705 | 5.106 | 17.09 |
| 286 | 661 | NON IBD | NON IBD | 12.049 | 16.705 | 2.273 | 7.56 |
| 287 | 663 | CD | IBD | 9.606 | 16.705 | 89.138 | 61.33 |
| 288 | 667 | UC | IBD | 27.762 | 16.705 | 4.723 | 10.12 |
| 289 | 668 | UC | IBD | 9.328 | 16.705 | 2.509 | 8.84 |
| 290 | 669 | CD | IBD | 14.881 | 16.705 | 1.860 | 11.31 |
| 291 | 672 | UC | IBD | 116.380 | 16.705 | 4.634 | 19.16 |
| 292 | 678 | CD | IBD | 9.717 | 16.705 | 2.037 | 17.43 |
| 293 | 679 | CD | IBD | 78.956 | 16.705 | 0.974 | 9.78 |
| 294 | 681 | UC | IBD | 8.329 | 16.705 | 1.771 | 16.25 |
| 295 | 702 | CD | IBD | 6.441 | 16.705 | 1.033 | 2.57 |
| 296 | 703 | CD | IBD | 18.656 | 16.705 | 87.426 | 81.04 |
| 297 | 704 | UC | IBD | 33.981 | 16.705 | 11.959 | 24.79 |
| 298 | 705 | CD | IBD | 35.702 | 16.705 | 16.102 | 23.65 |
| 299 | 706 | UC | IBD | 10.161 | 16.705 | 122.505 | 87.7 |
| 300 | 707 | UC | IBD | 12.993 | 16.705 | 4.175 | 18.02 |
| 301 | 709 | CD | IBD | 42.754 | 16.705 | 60.923 | 71.46 |
| 302 | 711 | IBS | NON IBD | 17.990 | 16.705 | 7.094 | 15.51 |
| 303 | 712 | CD | IBD | 19.267 | 16.705 | 38.449 | 38.57 |
| 304 | 714 | CD | IBD | 74.014 | 16.705 | 1.820 | 3.85 |
| 305 | 716 | UC | IBD | 127.263 | 16.705 | 5.618 | 12 |
| 306 | 717 | CD | IBD | 11.105 | 16.705 | 62.398 | 37.83 |
| 307 | 718 | UC | IBD | 34.703 | 16.705 | 5.085 | 33.09 |
| 308 | 719 | CD | IBD | 23.320 | 16.705 | 5.304 | 12.89 |
| 309 | 720 | CD | IBD | 38.701 | 16.705 | 165.851 | 115.85 |
| 310 | 721 | UC | IBD | 101.444 | 16.705 | 1.507 | 4.64 |
| 311 | 725 | IBS | NON IBD | 16.687 | 23.307 | 3.296 | 8.99 |
| 312 | 727 | CD | IBD | 16.872 | 23.307 | 2.103 | 22.75 |
| 313 | 728 | CD | IBD | 36.761 | 23.307 | 8.600 | 8.29 |
| 314 | 729 | UC | IBD | 94.828 | 23.307 | 2.103 | 7.48 |
| 315 | 730 | CD | IBD | 15.517 | 23.307 | 12.084 | 10.52 |
| 316 | 732 | UC | IBD | 18.350 | 23.307 | 1.507 | 7.33 |
| 317 | 733 | CD | IBD | 19.150 | 23.307 | 71.124 | 31.03 |
| 318 | 735 | UC | IBD | 41.010 | 23.307 | 3.453 | 11.44 |
| 319 | 736 | CD | IBD | 14.224 | 23.307 | 142.655 | 72.03 |
| 320 | 737 | NON IBD | NON IBD | 5.788 | 23.307 | −0.628 | 9.91 |
| 321 | 738 | NON IBD | NON IBD | 10.776 | 23.307 | 1.255 | 6.48 |
| 322 | 739 | UC | IBD | 14.840 | 23.307 | 6.403 | 5.87 |
| 323 | 740 | NON IBD | NON IBD | 14.286 | 23.307 | 5.116 | 18.83 |
| 324 | 741 | CD | IBD | 57.389 | 23.307 | 113.308 | 205.71 |
| 325 | 742 | UC | IBD | 33.744 | 23.307 | 4.018 | 7.41 |
| 326 | 743 | UC | IBD | 26.478 | 23.307 | 2.291 | 8.67 |
| 327 | 744 | NON IBD | NON IBD | 11.576 | 23.307 | 0.220 | 10.87 |
| 328 | 745 | UC | IBD | 36.392 | 23.307 | −0.157 | 2.48 |
| 329 | 746 | IBS | NON IBD | 19.150 | 23.307 | 3.013 | 4.6 |
| 330 | 747 | NON IBD | NON IBD | 15.702 | 23.307 | 0.471 | 9.29 |
| 331 | 748 | CD | IBD | 18.350 | 23.307 | 0.471 | 10.68 |
| 332 | 752 | UC | IBD | 86.084 | 23.307 | 9.856 | 5.17 |
| 333 | 753 | CD | IBD | 19.212 | 23.307 | 71.030 | 31.03 |
| 334 | 754 | UC | IBD | 23.584 | 23.307 | 3.986 | 2.52 |
| 335 | 755 | CD | IBD | 57.143 | 23.307 | 18.613 | 41.49 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 336 | 756 | CD | IBD | 19.951 | 23.307 | 210.264 | 157.55 |
| 337 | 758 | CD | IBD | 11.761 | 23.307 | 53.233 | 64.84 |
| 338 | 760 | UC | IBD | 35.160 | 23.307 | 17.420 | 33.03 |
| 339 | 761 | CONTROL | NON IBD | 26.152 | 20.930 | 1.682 | 7.67 |
| 340 | 762 | UC | IBD | 47.260 | 20.930 | 2.548 | 7.98 |
| 341 | 763 | CD | IBD | 29.016 | 20.930 | 40.987 | 10.6 |
| 342 | 764 | CONTROL | NON IBD | 24.159 | 20.930 | 2.035 | 6.94 |
| 343 | 767 | IBS | NON IBD | 17.995 | 20.930 | 38.776 | 27.37 |
| 344 | 768 | NON IBD | NON IBD | 17.435 | 20.930 | 14.245 | 33.41 |
| 345 | 769 | CD | IBD | 19.614 | 20.930 | 1.266 | 2.37 |
| 346 | 770 | UC | IBD | 52.179 | 20.930 | 2.964 | 5.22 |
| 347 | 771 | UC | IBD | 52.428 | 20.930 | 11.489 | 21.22 |
| 348 | 773 | UC | IBD | 38.854 | 20.930 | 26.678 | 31.49 |
| 349 | 802 | NON IBD | NON IBD | 18.182 | 20.930 | 7.435 | 15.91 |
| 350 | 803 | CD | IBD | 42.403 | 20.930 | 82.583 | 89.88 |
| 351 | 804 | NON IBD | NON IBD | 16.438 | 20.930 | 1.234 | 8.52 |
| 352 | 805 | CD | IBD | 63.263 | 20.930 | 34.321 | 75.73 |
| 353 | 806 | CD | IBD | 20.735 | 20.930 | 46.803 | 65.15 |
| 354 | 809 | UC | IBD | 81.133 | 20.930 | 1.009 | 4.48 |
| 355 | 810 | CD | IBD | 25.716 | 20.930 | 104.054 | 62.92 |
| 356 | 811 | CD | IBD | 15.567 | 20.930 | 76.334 | 64.38 |
| 357 | 813 | UC | IBD | 51.681 | 20.930 | 0.641 | 8.23 |
| 358 | 814 | CD | IBD | 18.182 | 20.930 | 26.598 | 68.68 |
| 359 | 816 | CD | IBD | 24.844 | 20.930 | 10.880 | 27.28 |
| 360 | 817 | UC | IBD | 33.686 | 20.930 | 1.394 | 9.78 |
| 361 | 820 | UC | IBD | 31.756 | 20.930 | 5.704 | 13.15 |
| 362 | 823 | UC | IBD | 23.848 | 20.930 | 1.058 | 4.5 |
| 363 | 828 | CD | IBD | 19.676 | 20.930 | 35.347 | 105.74 |
| 364 | 830 | UC | IBD | 24.222 | 20.930 | 1.859 | 9.63 |
| 365 | 831 | UC | IBD | 72.727 | 20.930 | 4.278 | 13.47 |
| 366 | 832 | UC | IBD | 85.367 | 20.930 | 10.399 | 8.05 |
| 367 | 833 | UC | IBD | 18.804 | 20.930 | 2.115 | 19.43 |
| 368 | 834 | UC | IBD | 26.588 | 20.930 | 4.198 | 14.73 |
| 369 | 835 | CD | IBD | 13.138 | 20.930 | 5.405 | 55.37 |
| 370 | 836 | CD | IBD | 16.376 | 20.930 | 39.533 | 23.98 |
| 371 | 837 | NON IBD | NON IBD | 6.351 | 20.930 | 12.597 | 36.86 |
| 372 | 839 | CD | IBD | 16.252 | 20.930 | 118.140 | 145.7 |
| 373 | 841 | UC | IBD | 15.567 | 20.930 | 1.619 | 7.7 |
| 374 | 862 | CD | IBD | 20.152 | 15.673 | 93.814 | 111.16 |
| 375 | 863 | CD | IBD | 38.431 | 15.673 | 2.410 | 34.92 |
| 376 | 874 | CD | IBD | 9.496 | 15.673 | 29.593 | 62.83 |
| 377 | 875 | CD | IBD | 50.111 | 15.673 | 12.453 | 12.57 |
| 378 | 905 | CD | IBD | 34.909 | 15.673 | 5.316 | 5.59 |
| 379 | 906 | CD | IBD | 34.641 | 15.673 | 66.149 | 56.76 |
| 380 | 914 | CD | IBD | 33.972 | 15.673 | 12.199 | 14.98 |
| 381 | 929 | CD | IBD | 9.184 | 15.673 | 32.325 | 19.78 |
| 382 | 930 | UC | IBD | 33.839 | 15.673 | 5.651 | 16.69 |
| 383 | 939 | UC | IBD | 114.044 | 15.673 | 2.825 | 7.33 |
| 384 | 940 | IBS | NON IBD | 2.987 | 15.673 | 3.656 | 4.45 |
| 385 | 942 | CD | IBD | 13.286 | 15.673 | 81.427 | 51.87 |
| 386 | 943 | CD | IBD | 4.547 | 15.673 | 3.990 | 5.91 |
| 387 | 945 | CD | IBD | 12.158 | 11.390 | 6.856 | 21.79 |
| 388 | 947 | CD | IBD | 5.410 | 11.390 | 26.312 | 69.17 |
| 389 | 948 | UC | IBD | 20.790 | 11.390 | 6.387 | 8.38 |
| 390 | 949 | UC | IBD | 132.219 | 11.390 | 3.508 | 9.13 |
| 391 | 950 | CD | IBD | 9.666 | 11.390 | 3.575 | 7.12 |
| 392 | 951 | UC | IBD | 45.350 | 11.390 | 13.484 | 33.78 |
| 393 | 954 | CD | IBD | 11.307 | 11.390 | 39.743 | 38.29 |
| 394 | 955 | UC | IBD | 23.647 | 11.390 | 1.366 | 8.29 |
| 395 | 957 | UC | IBD | 18.541 | 11.390 | 4.874 | 9.17 |
| 396 | 959 | IBS | NON IBD | 10.274 | 11.390 | 4.379 | 4.36 |
| 397 | 961 | UC | IBD | 11.611 | 11.390 | 0.951 | 17.45 |
| 398 | 962 | UC | IBD | 12.584 | 11.390 | 0.589 | 7.12 |
| 399 | 963 | UC | IBD | 19.939 | 11.390 | 2.906 | 30.43 |
| 400 | 964 | UC | IBD | 38.116 | 11.390 | 3.696 | 11.70 |
| 401 | 965 | IBS | NON IBD | 6.505 | 11.390 | 1.861 | 2.82 |
| 402 | 966 | IBS | NON IBD | 6.505 | 11.390 | 11.061 | 10.45 |
| 403 | 967 | CD | IBD | 7.234 | 11.390 | 27.009 | 102.39 |
| 404 | 968 | NON IBD | NON IBD | 18.541 | 11.390 | 4.111 | 9.36 |
| 405 | 969 | IBS | NON IBD | 12.462 | 11.390 | 6.709 | 21.60 |
| 406 | 970 | CD | IBD | 29.119 | 11.390 | 76.995 | 40.16 |
| 407 | 971 | CD | IBD | 19.453 | 11.390 | 91.885 | 74.55 |
| 408 | 972 | CD | IBD | 11.672 | 11.390 | 43.198 | 104.83 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 409 | 973 | UC | IBD | 29.240 | 11.390 | 2.384 | 9.65 |
| 410 | 974 | UC | IBD | 21.033 | 11.390 | 6.909 | 9.93 |
| 411 | 979 | CD | IBD | 26.261 | 11.390 | 88.431 | 166.66 |
| 412 | 1003 | NON IBD | NON IBD | 4.216 | 10.493 | 3.878 | 13.01 |
| 413 | 1004 | CD | IBD | 3.972 | 10.493 | 7.574 | 18.13 |
| 414 | 1005 | CD | IBD | 27.767 | 10.493 | 12.185 | 44.66 |
| 415 | 1007 | CD | IBD | 11.755 | 10.493 | 0.763 | 9.02 |
| 416 | 1008 | UC | IBD | 38.346 | 10.493 | 25.683 | 13.29 |
| 417 | 1009 | UC | IBD | 5.310 | 10.493 | 4.031 | 11.30 |
| 418 | 1011 | NON IBD | NON IBD | 5.918 | 10.493 | 3.791 | 4.64 |
| 419 | 1014 | CD | IBD | 33.847 | 10.493 | 3.901 | 7.71 |
| 420 | 1017 | NON IBD | NON IBD | 2.351 | 10.493 | 0.069 | 2.87 |
| 421 | 1020 | UC | IBD | 10.215 | 10.493 | 3.846 | 17.73 |
| 422 | 1022 | CONTROL | NON IBD | 6.972 | 10.493 | 3.878 | 16.03 |
| 423 | 1025 | UC | IBD | 40.940 | 10.493 | 2.541 | 34.58 |
| 424 | 1026 | CONTROL | NON IBD | 11.715 | 10.493 | 7.574 | 59.29 |
| 425 | 1029 | NON IBD | NON IBD | 4.580 | 10.493 | 6.991 | 11.24 |
| 426 | 1031 | CONTROL | NON IBD | 5.432 | 10.493 | 14.558 | 7.66 |
| 427 | 1032 | NON IBD | NON IBD | 1.500 | 10.493 | 3.063 | 12.84 |
| 428 | 1034 | WEGENER'S | NON IBD | 76.976 | 10.493 | 9.463 | 25.99 |
| 429 | 1035 | CONTROL | NON IBD | 9.972 | 10.493 | 15.726 | 32.48 |
| 430 | 1040 | UC | IBD | 28.334 | 10.493 | 3.118 | 15.00 |
| 431 | 1042 | UC | IBD | 70.409 | 10.493 | 4.477 | 11.70 |
| 432 | 1043 | UC | IBD | 16.214 | 10.493 | 7.595 | 10.05 |
| 433 | 1044 | UC | IBD | 36.927 | 10.493 | 1.538 | 8.51 |
| 434 | 1045 | UC | IBD | 20.916 | 10.493 | 6.139 | 14.55 |
| 435 | 1046 | UC | IBD | 31.658 | 10.493 | 3.390 | 8.51 |
| 436 | 1047 | UC | IBD | 121.078 | 10.493 | 41.656 | 22.63 |
| 437 | 1048 | UC | IBD | 46.500 | 10.493 | 7.142 | 12.84 |
| 438 | 1048 | UC | IBD | 46.453 | 10.493 | 3.970 | 12.84 |
| 439 | 1049 | UC | IBD | 110.661 | 10.493 | 38.580 | 25.70 |
| 440 | 1050 | UC | IBD | 21.970 | 10.493 | 3.063 | 3.50 |
| 441 | 1051 | UC | IBD | 44.751 | 10.493 | 1.058 | 18.46 |
| 442 | 1052 | CD | IBD | 29.179 | 11.390 | 7.183 | 39.51 |
| 443 | 1054 | UC | IBD | 9.688 | 10.493 | 4.162 | 19.40 |
| 444 | 1055 | UC | IBD | 7.621 | 10.493 | 43.662 | 35.22 |
| 445 | 1056 | UC | IBD | 61.411 | 10.493 | 21.796 | 79.56 |
| 446 | 1057 | CONTROL | NON IBD | 8.188 | 10.493 | 1.799 | 12.03 |
| 447 | 1058 | UC | IBD | 16.052 | 10.493 | 12.842 | 66.21 |
| 448 | 1059 | UC | IBD | 10.230 | 12.074 | 16.852 | 19.23 |
| 449 | 1061 | UC | IBD | 29.967 | 12.074 | 5.439 | 48.63 |
| 450 | 1062 | UC | IBD | 6.820 | 12.074 | 0.247 | 5.33 |
| 451 | 1063 | UC | IBD | 3.148 | 12.074 | 3.214 | 8.46 |
| 452 | 1064 | UC | IBD | 10.303 | 12.074 | 2.362 | 10.49 |
| 453 | 1066 | UC | IBD | 40.852 | 12.074 | 8.680 | 14.01 |
| 454 | 1067 | UC | IBD | 11.148 | 12.074 | 1.112 | 3.96 |
| 455 | 1068 | UC | IBD | 11.803 | 12.074 | 4.299 | 6.26 |
| 456 | 1069 | UC | IBD | 15.279 | 12.074 | 1.387 | 2.47 |
| 457 | 1070 | UC | IBD | 5.508 | 12.074 | 1.195 | 7.53 |
| 458 | 1071 | UC | IBD | 2.885 | 12.074 | 6.167 | 10.71 |
| 459 | 1072 | UC | IBD | 70.230 | 12.074 | 28.554 | 18.46 |
| 460 | 1073 | UC | IBD | 25.508 | 12.074 | 3.379 | 9.56 |
| 461 | 1074 | UC | IBD | 48.131 | 12.074 | 8.721 | 12.97 |
| 462 | 1075 | CONTROL | NON IBD | 6.557 | 12.074 | 5.700 | 13.02 |
| 463 | 1076 | CONTROL | NON IBD | 3.410 | 12.074 | 0.4.81 | 6.87 |
| 464 | 1077 | UC | IBD | 29.605 | 11.390 | 7.760 | 8.08 |
| 465 | 1080 | CONTROL | NON IBD | 3.607 | 12.074 | 2.884 | 15.44 |
| 466 | 1081 | UC | IBD | 45.115 | 12.074 | 2.474 | 9.45 |
| 467 | 1106 | UC | IBD | 13.435 | 11.390 | 7.664 | 6.92 |
| 468 | 1107 | UC | IBD | 45.410 | 11.390 | 10.507 | 20.88 |
| 469 | 1109 | UC | IBD | 19.149 | 11.390 | 10.739 | 19.07 |
| 470 | 1110 | UC | IBD | 137.812 | 11.390 | 18.189 | 12.55 |
| 471 | 1111 | UC | IBD | 20.182 | 11.390 | 8.038 | 49.95 |
| 472 | 1112 | UC | IBD | 63.100 | 11.390 | 1.109 | 19.12 |
| 473 | 1114 | CONTROL | NON IBD | 12.280 | 11.390 | 25.052 | 10.00 |
| 474 | 1135 | CONTROL | NON IBD | 7.086 | 11.931 | 2.270 | 11.25 |
| 475 | 1136 | CONTROL | NON IBD | 11.118 | 11.931 | 1.062 | 67.24 |
| 476 | 1139 | CONTROL | NON IBD | 9.346 | 11.931 | 21.020 | 34.18 |
| 477 | 1141 | CONTROL | NON IBD | 11.973 | 11.931 | 5.227 | 5.49 |
| 478 | 1143 | CONTROL | NON IBD | 19.181 | 11.931 | 24.465 | 8.46 |
| 479 | 1201 | CONTROL | NON IBD | 8.430 | 11.931 | 11.091 | 40.82 |
| 480 | 1207 | CONTROL | NON IBD | 13.561 | 11.931 | 5.115 | 22.20 |
| 481 | 1208 | CONTROL | NON IBD | 13.500 | 11.931 | 15.423 | 26.45 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 482 | 1209 | CONTROL | NON IBD | 19.976 | 11.931 | 5.271 | 28.89 |
| 483 | 1227 | UC | IBD | 112.645 | 11.931 | 1.200 | 14.79 |
| 484 | 1229 | CONTROL | NON IBD | 12.523 | 11.931 | 36.391 | 23.02 |
| 485 | 1230 | CONTROL | NON IBD | 5.987 | 11.931 | 3.079 | 9.38 |
| 486 | 1303 | CONTROL | NON IBD | 7.880 | 11.931 | 4.410 | 12.96 |
| 487 | 1305 | CONTROL | NON IBD | 8.369 | 11.931 | 1.527 | 2.13 |
| 488 | 1307 | CONTROL | NON IBD | 9.835 | 11.931 | 9.982 | 17.15 |
| 489 | 1308 | UC | IBD | 20.648 | 11.931 | 19.794 | 10.29 |
| 490 | 1309 | CONTROL | NON IBD | 11.546 | 11.931 | 20.420 | 50.30 |
| 491 | 1323 | CONTROL | NON IBD | 11.607 | 11.931 | 4.345 | 9.15 |
| 492 | 1326 | CONTROL | NON IBD | 17.288 | 11.931 | 5.454 | 9.53 |
| 493 | 1330 | CONTROL | NON IBD | 5.070 | 11.931 | 4.736 | 20.73 |
| 494 | 1334 | CONTROL | NON IBD | 11.057 | 11.931 | 1.253 | 2.90 |
| 495 | 1408 | CONTROL | NON IBD | 12.034 | 11.931 | 30.089 | 13.11 |
| 496 | 1413 | CONTROL | NON IBD | 7.941 | 11.931 | 3.719 | 5.11 |
| 497 | 1419 | CONTROL | NON IBD | 11.057 | 11.931 | 3.732 | 82.70 |
| 498 | 1420 | CONTROL | NON IBD | 7.636 | 11.931 | 5.493 | 9.53 |
| 499 | 1427 | UC | IBD | 97.373 | 11.931 | 6.080 | 17.61 |
| 500 | 1436 | CONTROL | NON IBD | 21.503 | 11.931 | 1.840 | 12.50 |
| 501 | 1440 | UC | IBD | 35.858 | 11.931 | 36.443 | 15.85 |
| 502 | 1501 | UC | IBD | 109.312 | 12.074 | 5.806 | 11.36 |
| 503 | 1505 | UC | IBD | 131.869 | 12.074 | 2.518 | 5.95 |
| 504 | 1506 | CD | IBD | 10.623 | 12.074 | 85.530 | 46.27 |
| 505 | 1507 | CD | IBD | 2.230 | 12.074 | 101.096 | 46.27 |
| 506 | 1511 | CD | IBD | 3.738 | 12.074 | 5.741 | 10.29 |
| 507 | 1514 | UC | IBD | 159.279 | 12.074 | 3.510 | 28.28 |
| 508 | 1517 | CD | IBD | 43.869 | 12.074 | 16.310 | 13.95 |
| 509 | 1519 | UC | IBD | 79.475 | 12.074 | 4.684 | 11.28 |
| 510 | 1603 | CD | IBD | 2.623 | 12.074 | 98.904 | 39.94 |
| 511 | 1604 | CD | IBD | 8.197 | 12.074 | 47.651 | 74.09 |
| 512 | 1605 | CD | IBD | 10.557 | 12.074 | 16.127 | 30.03 |
| 513 | 1607 | CD | IBD | 10.623 | 12.074 | 10.626 | 11.28 |
| 514 | 1608 | CD | IBD | 3.213 | 12.074 | 6.971 | 27.82 |
| 515 | 1610 | CD | IBD | 6.557 | 12.074 | 0.368 | 0.91 |
| 516 | 1611 | CD | IBD | 6.623 | 12.074 | 97.540 | 77.97 |
| 517 | 1613 | CD | IBD | 15.157 | 22.230 | 73.203 | 33.61 |
| 518 | 1614 | CD | IBD | 22.410 | 22.230 | 16.171 | 16.23 |
| 519 | 1616 | CD | IBD | 8.365 | 22.230 | 96.712 | 63.34 |
| 520 | 1618 | CD | IBD | 12.164 | 22.230 | 1.454 | 3.28 |
| 521 | 1619 | CD | IBD | 7.406 | 22.230 | 54.002 | 27.13 |
| 522 | 1620 | CD | IBD | 17.114 | 22.230 | 6.346 | 36.52 |
| 523 | 1623 | CONTROL | NON IBD | 13.738 | 22.230 | 11.442 | 23.18 |
| 524 | 1625 | CD | IBD | 21.757 | 22.230 | 0.000 | 8.78 |
| 525 | 1627 | CD | IBD | 61.704 | 22.230 | 0.775 | 5.27 |
| 526 | 1628 | CD | IBD | 6.293 | 22.230 | 8.330 | 13.11 |
| 527 | 1632 | CONTROL | NON IBD | 8.135 | 22.230 | 97.214 | 108.62 |
| 528 | 1634 | CD | IBD | 6.370 | 22.230 | 67.536 | 16.35 |
| 529 | 1636 | CONTROL | NON IBD | 7.483 | 22.230 | 0.489 | 6.87 |
| 530 | 1638 | CONTROL | NON IBD | 7.713 | 22.230 | 2.786 | 8.78 |
| 531 | 1639 | CD | IBD | 12.394 | 22.230 | 0.802 | 9.56 |
| 532 | 1640 | CD | IBD | 8.596 | 22.230 | 33.564 | 34.06 |
| 533 | 1712 | UC | IBD | 154.144 | 22.230 | 0.000 | 3.39 |
| 534 | 1713 | CD | IBD | 5.871 | 22.230 | 3.030 | 11 |
| 535 | 1714 | CD | IBD | 11.704 | 22.230 | 44.775 | 27.16 |
| 536 | 1728 | CONTROL | NON IBD | 13.085 | 22.230 | 1.807 | 11.04 |
| 537 | 1805 | UC | IBD | 92.748 | 22.230 | −1.957 | 7.73 |
| 538 | 1811 | UC | IBD | 25.058 | 22.230 | 5.762 | 21.73 |
| 539 | 1812 | CD | IBD | 12.164 | 22.230 | 3.085 | 19.08 |
| 540 | 1813 | CONTROL | NON IBD | 5.833 | 22.230 | −0.544 | 19.2 |
| 541 | 1817 | CONTROL | NON IBD | 4.375 | 22.230 | 0.272 | 5.77 |
| 542 | 1914 | CONTROL | NON IBD | 15.925 | 22.230 | 10.096 | 8.86 |
| 543 | 1939 | UC | IBD | 11.282 | 22.230 | 1.508 | 7.96 |
| 544 | 1945 | CD | IBD | 11.972 | 22.230 | 19.541 | 24.85 |
| 545 | 2002 | UC | IBD | 52.724 | 22.230 | 57.236 | 18.73 |
| 546 | 2010 | UC | IBD | 35.125 | 11.931 | 8.588 | 10.65 |
| 547 | 2017 | CD | IBD | 11.484 | 11.931 | 22.761 | 16.54 |
| 548 | 2025 | UC | IBD | 31.643 | 11.931 | −0.707 | 7.06 |
| 549 | 2027 | UC | IBD | 92.059 | 11.931 | 7.949 | 23.60 |
| 550 | 2034 | CD | IBD | 11.240 | 11.931 | 76.996 | 32.31 |
| 551 | 2037 | CD | IBD | 102.671 | 20.016 | 2.603 | 11.74 |
| 552 | 2048 | CD | IBD | 19.565 | 20.016 | 34.830 | 117.25 |
| 553 | 2049 | UC | IBD | 125.839 | 20.016 | 3.284 | 18.30 |
| 554 | 2050 | UC | IBD | 63.043 | 20.016 | 3.231 | 4.37 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 555 | 2152 | CD | IBD | 32.547 | 20.016 | 10.201 | |
| 556 | 2203 | CD | IBD | 13.292 | 20.016 | 5.345 | 10.97 |
| 557 | 2205 | CD | IBD | 14.286 | 20.016 | 26.638 | 31.35 |
| 558 | 2228 | CONTROL | NON IBD | 10.870 | 20.016 | 3.668 | 9.05 |
| 559 | 2232 | CD | IBD | 28.882 | 20.016 | 118.812 | 110.53 |
| 560 | 2233 | UC | IBD | 49.814 | 20.016 | 8.245 | 15.17 |
| 561 | 2234 | UC | IBD | 76.211 | 20.016 | 0.000 | 5.56 |
| 562 | 2236 | CONTROL | NON IBD | 8.944 | 20.016 | 1.310 | 5.48 |
| 563 | 2237 | CD | IBD | 120.124 | 20.016 | 20.437 | 47.36 |
| 564 | 2240 | CD | IBD | 30.932 | 20.016 | 135.179 | 97.72 |
| 565 | 2241 | CD | IBD | 24.845 | 20.016 | 108.489 | 53.72 |
| 566 | 2243 | CD | IBD | 10.870 | 20.016 | 66.498 | 20.22 |
| 567 | 2244 | CD | IBD | 22.609 | 20.016 | 2.725 | 3.60 |
| 568 | 2250 | UC | IBD | 78.634 | 20.016 | 8.611 | 14.85 |
| 569 | 2252 | UC | IBD | 74.161 | 20.016 | 6.393 | 15.77 |
| 570 | 2253 | UC | IBD | 26.025 | 20.016 | 0.838 | 6.24 |
| 571 | 2254 | CD | IBD | 14.907 | 20.016 | 4.175 | 7.37 |
| 572 | 2256 | CD | IBD | 18.012 | 20.016 | 3.843 | 17.01 |
| 573 | 2257 | CD | IBD | 31.553 | 20.016 | 54.603 | 33.55 |
| 574 | 2259 | CD | IBD | 20.000 | 20.016 | 132.804 | 120.82 |
| 575 | 2261 | CD | IBD | 28.199 | 20.016 | 114.690 | 91.47 |
| 576 | 2270 | NON IBD | NON IBD | 20.559 | 20.016 | 11.651 | 7.57 |
| 577 | 2303 | CD | IBD | 7.329 | 20.016 | 4.000 | 13.81 |
| 578 | 2314 | UC | IBD | 93.665 | 20.016 | 6.847 | 5.48 |
| 579 | 2315 | CONTROL | NON IBD | 11.242 | 20.016 | 8.157 | 6.93 |
| 580 | 2318 | UC | IBD | 5.031 | 20.016 | 50.515 | 22.18 |
| 581 | 2358 | CD | IBD | 14.806 | 25.355 | 17.782 | 23.70 |
| 582 | 2364 | UC | IBD | 32.524 | 25.355 | 4.873 | 8.85 |
| 583 | 2368 | UC | IBD | 10.194 | 25.355 | 60.541 | 67.69 |
| 584 | 2406 | UC | IBD | 94.053 | 25.355 | 11.913 | 15.33 |
| 585 | 2407 | CD | IBD | 15.291 | 25.355 | 13.205 | 57.89 |
| 586 | 2408 | CD | IBD | 40.473 | 25.355 | 20.035 | 18.69 |
| 587 | 2420 | CD | IBD | 179.612 | 25.355 | 4.419 | 22.38 |
| 588 | 2422 | CD | IBD | 11.529 | 25.355 | 4.603 | 16.09 |
| 589 | 2427 | UC | IBD | 13.046 | 25.355 | 3.217 | 10.93 |
| 590 | 2429 | UC | IBD | 285.012 | 25.355 | 4.795 | 20.69 |
| 591 | 2435 | UC | IBD | 56.675 | 25.355 | 5.945 | 12.14 |
| 592 | 2437 | CD | IBD | 12.197 | 25.355 | 2.896 | 22.49 |
| 593 | 2438 | UC | IBD | 165.473 | 25.355 | 2.283 | 26.24 |
| 594 | 2439 | CD | IBD | 142.901 | 25.355 | 17.880 | 37.63 |
| 595 | 2442 | UC | IBD | 19.478 | 25.355 | 112.226 | 159.45 |
| 596 | 2447 | UC | IBD | 80.886 | 25.355 | 0.291 | 23.01 |
| 597 | 2451 | CD | IBD | 26.699 | 25.355 | 14.003 | 75.11 |
| 598 | 2452 | UC | IBD | 22.209 | 25.355 | 16.210 | 17.02 |
| 599 | 2453 | UC | IBD | 123.544 | 25.355 | 51.601 | 51.27 |
| 600 | 2454 | CD | IBD | 22.573 | 25.355 | 3.034 | 24.06 |
| 601 | 2456 | UC | IBD | 20.813 | 25.355 | 110.694 | 64.62 |
| 602 | 2464 | CD | IBD | 62.864 | 25.355 | 64.961 | 146.93 |
| 603 | 2466 | CD | IBD | 21.905 | 25.355 | 31.592 | 88.16 |
| 604 | 2467 | UC | IBD | 41.080 | 25.355 | 3.080 | 23.54 |
| 605 | 2473 | CD | IBD | 21.516 | 12.657 | 21.327 | 15.52 |
| 606 | 2475 | UC | IBD | 21.890 | 12.657 | 17.497 | 54.27 |
| 607 | 2477 | UC | IBD | 46.716 | 12.657 | 3.049 | 23.09 |
| 608 | 2503 | UC | IBD | 30.112 | 12.657 | 1.593 | 10.72 |
| 609 | 2506 | UC | IBD | 71.276 | 12.657 | 0.919 | 16.19 |
| 610 | 2507 | UC | IBD | 76.241 | 12.657 | 7.783 | 35.01 |
| 611 | 2509 | CD | IBD | 13.454 | 12.657 | 84.036 | 80.88 |
| 612 | 2510 | CD | IBD | 16.231 | 12.657 | 107.722 | 138.91 |
| 613 | 2511 | CD | IBD | 16.551 | 12.657 | 25.770 | 23.46 |
| 614 | 2514 | UC | IBD | 24.933 | 12.657 | 0.000 | 12.59 |
| 615 | 2516 | UC | IBD | 104.965 | 12.657 | 0.797 | 10.49 |
| 616 | 2517 | UC | IBD | 38.174 | 12.657 | 2.237 | 32.01 |
| 617 | 2520 | CD | IBD | 23.599 | 12.657 | 9.622 | 21.06 |
| 618 | 2521 | UC | IBD | 40.790 | 12.657 | 88.096 | 88.98 |
| 619 | 2522 | UC | IBD | 24.372 | 13.499 | 1.731 | 21.96 |
| 620 | 2533 | UC | IBD | 39.349 | 12.657 | 1.593 | 15.22 |
| 621 | 2535 | CD | IBD | 9.343 | 12.657 | 0.950 | 6.45 |
| 622 | 2537 | UC | IBD | 69.301 | 12.657 | 0.000 | 4.57 |
| 623 | 2538 | CD | IBD | 4.849 | 20.382 | 2.978 | 7.5 |
| 624 | 2540 | CD | IBD | 10.358 | 12.657 | 102.712 | 132.08 |
| 625 | 2541 | UC | IBD | 8.596 | 12.657 | 2.405 | 16.49 |
| 626 | 2542 | UC | IBD | 38.334 | 12.657 | 5.592 | 19.85 |
| 627 | 2543 | UC | IBD | 150.721 | 20.382 | 7.531 | 24.76 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 628 | 2555 | CD | IBD | 96.003 | 20.382 | 0.915 | 14.87 |
| 629 | 2557 | UC | IBD | 16.710 | 20.382 | 1.774 | 11.76 |
| 630 | 2559 | UC | IBD | 140.105 | 20.382 | 5.912 | 20.75 |
| 631 | 2560 | CD | IBD | 9.174 | 20.382 | 7.573 | 15.7 |
| 632 | 2561 | CD | IBD | 5.177 | 20.382 | 3.533 | 23.51 |
| 633 | 2562 | CD | IBD | 6.750 | 20.382 | 10.206 | 8.71 |
| 634 | 2563 | CD | IBD | 17.369 | 20.382 | 16.258 | 6.78 |
| 635 | 2564 | UC | IBD | 8.257 | 20.382 | 0.479 | 5.05 |
| 636 | 2569 | CD | IBD | 29.030 | 20.382 | 5.870 | 24.2 |
| 637 | 2570 | UC | IBD | 9.183 | 12.657 | 2.365 | 11.89 |
| 638 | 2572 | UC | IBD | 109.877 | 12.657 | 83.784 | 39.83 |
| 639 | 2573 | UC | IBD | 71.223 | 12.657 | 3.773 | 39.56 |
| 640 | 2575 | CD | IBD | 15.750 | 12.657 | 6.461 | 12.45 |
| 641 | 2576 | UC | IBD | 65.350 | 12.657 | 1.478 | 16.39 |
| 642 | 2577 | CD | IBD | 11.426 | 12.657 | 101.788 | 22.75 |
| 643 | 2578 | CD | IBD | 21.244 | 13.499 | 82.630 | 51.45 |
| 644 | 2579 | UC | IBD | 68.830 | 13.499 | 0.338 | 4.36 |
| 645 | 2601 | UC | IBD | 76.555 | 13.499 | 9.333 | 14.25 |
| 646 | 2602 | CD | IBD | 5.253 | 13.499 | 45.861 | 31.54 |
| 647 | 2605 | UC | IBD | 129.703 | 13.499 | 1.408 | 7.75 |
| 648 | 2607 | UC | IBD | 66.242 | 13.499 | 3.125 | 7.05 |
| 649 | 2608 | UC | IBD | 16.261 | 13.499 | 4.842 | 7.12 |
| 650 | 2609 | CD | IBD | 13.055 | 13.499 | 26.675 | 34.92 |
| 651 | 2610 | CD | IBD | 7.532 | 13.499 | 2.717 | 10.58 |
| 652 | 2611 | UC | IBD | 13.210 | 13.499 | 1.182 | 8.78 |
| 653 | 2612 | CD | IBD | 146.505 | 13.499 | 3.041 | 20.06 |
| 654 | 880585 | CONTROL | NON IBD | 12.536 | 8.283 | 1.244 | 28.8184 |
| 655 | 890037 | CONTROL | NON IBD | 5.364 | 8.283 | 1.168 | 13.5446 |
| 656 | 890361 | CONTROL | NON IBD | 6.356 | 8.283 | 1.206 | 3.8904 |
| 657 | 890550 | CONTROL | NON IBD | 3.907 | 8.283 | 8.517 | 8.9337 |
| 658 | 890581 | CONTROL | NON IBD | 14.985 | 8.283 | 2.450 | 4.755 |
| 659 | 890622 | CONTROL | NON IBD | 9.271 | 8.283 | 2.902 | 4.1786 |
| 660 | 890627 | CONTROL | NON IBD | 17.318 | 8.283 | 31.242 | 22.9106 |
| 661 | 900097 | CONTROL | NON IBD | 7.910 | 9.503 | 2.713 | 8.5014 |
| 662 | 900146 | CONTROL | NON IBD | 5.726 | 9.503 | 0.735 | 7.7809 |
| 663 | 900224 | CONTROL | NON IBD | 19.540 | 9.503 | 1.865 | 10.6628 |
| 664 | 900329 | CONTROL | NON IBD | 9.504 | 9.503 | 1.489 | 2.7377 |
| 665 | 900421 | CONTROL | NON IBD | 7.202 | 9.503 | 14.754 | 12.1037 |
| 666 | 900450 | CONTROL | NON IBD | 6.907 | 9.503 | 0.471 | 4.3227 |
| 667 | 900452 | CONTROL | NON IBD | 6.789 | 9.503 | 1.131 | 17.8674 |
| 668 | 900482 | CONTROL | NON IBD | 11.452 | 9.503 | 6.425 | 19.1642 |
| 669 | 900504 | CONTROL | NON IBD | 12.220 | 9.503 | 0.343 | 2.8184 |
| 670 | 900659 | CONTROL | NON IBD | 14.699 | 9.503 | 4.250 | 11.9503 |
| 671 | 900709 | CONTROL | NON IBD | 16.588 | 9.503 | 1.202 | 10.0338 |
| 672 | 900748 | CONTROL | NON IBD | 7.792 | 9.503 | 1.524 | 4.735 |
| 673 | 910039 | CONTROL | NON IBD | 4.723 | 9.503 | 3.713 | 5.2987 |
| 674 | 910042 | CONTROL | NON IBD | 4.959 | 9.503 | 3.155 | 30.5524 |
| 675 | 910056 | CONTROL | NON IBD | 13.872 | 9.503 | 1.760 | 13.3032 |
| 676 | 910095 | CONTROL | NON IBD | 14.876 | 9.503 | 0.515 | 11.7249 |
| 677 | 910101 | CONTROL | NON IBD | 13.991 | 9.503 | 2.576 | 30.5524 |
| 678 | 910104 | CONTROL | NON IBD | 17.119 | 9.503 | 3.069 | 3.6076 |
| 679 | 910108 | CONTROL | NON IBD | 9.622 | 9.503 | 1.717 | 6.3134 |
| 680 | 910156 | CONTROL | NON IBD | 3.011 | 9.503 | 1.996 | 6.5388 |
| 681 | 910214 | CONTROL | NON IBD | 6.966 | 9.503 | 0.622 | 7.779 |
| 682 | 910217 | CONTROL | NON IBD | 4.604 | 9.503 | 0.880 | 5.9751 |
| 683 | 910220 | CONTROL | NON IBD | 12.633 | 9.503 | 3.069 | 15.558 |
| 684 | 910234 | CONTROL | NON IBD | 12.279 | 9.503 | 5.216 | 117.1364 |
| 685 | 910561 | CONTROL | NON IBD | 11.393 | 9.503 | 5.646 | 2.2099 |
| 686 | 920028 | CONTROL | NON IBD | 15.821 | 9.503 | 1.695 | 11.5172 |
| 687 | 920056 | CONTROL | NON IBD | 12.102 | 9.503 | 2.284 | 4.2073 |
| 688 | 920142 | CONTROL | NON IBD | 9.858 | 9.503 | 5.789 | 36.2091 |
| 689 | 920184 | CONTROL | NON IBD | 9.792 | 11.138 | 7.163 | 6.3545 |
| 690 | 920258 | CONTROL | NON IBD | 4.036 | 11.138 | 4.077 | 9.0969 |
| 691 | 920260 | CONTROL | NON IBD | 6.706 | 11.138 | 4.481 | 6.2207 |
| 692 | 920264 | CONTROL | NON IBD | 9.080 | 11.138 | 3.343 | 3.5451 |
| 693 | 920302 | CONTROL | NON IBD | 6.944 | 11.138 | 4.555 | 6.1538 |
| 694 | 920346 | CONTROL | NON IBD | 12.226 | 11.138 | 10.670 | 52.3745 |
| 695 | 920448 | CONTROL | NON IBD | 10.564 | 11.138 | 4.353 | 5.3511 |
| 696 | 930031 | CONTROL | NON IBD | 12.997 | 11.138 | 1.635 | 5.9531 |
| 697 | 930182 | CONTROL | NON IBD | 4.392 | 11.138 | 5.197 | 12.9097 |
| 698 | 930184 | CONTROL | NON IBD | 2.967 | 11.138 | 2.204 | 31.505 |
| 699 | 930219 | CONTROL | NON IBD | 11.157 | 11.138 | 1.157 | 12.1739 |
| 700 | 930222 | CONTROL | NON IBD | 11.039 | 11.138 | 14.123 | 18.2608 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 701 | 930225 | CONTROL | NON IBD | 4.392 | 11.138 | 2.755 | 10.903 |
| 702 | 930228 | CONTROL | NON IBD | 2.849 | 11.138 | 4.463 | 7.4916 |
| 703 | 930243 | CONTROL | NON IBD | 10.148 | 11.138 | 0.680 | 9.3645 |
| 704 | 930266 | CONTROL | NON IBD | 4.273 | 11.138 | 9.605 | 16.321 |
| 705 | 930268 | CONTROL | NON IBD | 11.988 | 11.138 | 14.509 | 14.9163 |
| 706 | 930516 | CONTROL | NON IBD | 3.680 | 11.138 | 14.527 | 5.5518 |
| 707 | 940106 | CONTROL | NON IBD | 7.596 | 11.138 | 1.451 | 3.4782 |
| 708 | 950795 | CONTROL | NON IBD | 3.442 | 11.138 | 10.854 | 9.6321 |
| 709 | 950940 | CONTROL | NON IBD | 1.068 | 11.138 | 1.157 | 4.0133 |
| 710 | 860211 | CONTROL | NON IBD | 9.489 | 11.205 | 4.615 | 10.0094 |
| 711 | 860214 | CONTROL | NON IBD | 7.688 | 11.205 | 0.671 | 3.0217 |
| 712 | 870018 | CONTROL | NON IBD | 7.147 | 11.205 | 0.378 | 22.0018 |
| 713 | 880055 | CONTROL | NON IBD | 6.907 | 11.205 | 0.378 | 3.4938 |
| 714 | 880071 | CONTROL | NON IBD | 4.384 | 11.205 | 5.538 | 7.7431 |
| 715 | 880626 | CONTROL | NON IBD | 11.832 | 11.205 | 3.923 | 25.118 |
| 716 | 890061 | CONTROL | NON IBD | 4.745 | 11.205 | 0.441 | 1.8885 |
| 717 | 890163 | CONTROL | NON IBD | 8.468 | 11.205 | 5.496 | 31.1614 |
| 718 | 890308 | CONTROL | NON IBD | 8.724 | 8.754 | 0.399 | 2.2662 |
| 719 | 890353 | CONTROL | NON IBD | 15.608 | 8.754 | 3.147 | 6.3267 |
| 720 | 890362 | CONTROL | NON IBD | 7.003 | 8.754 | 1.575 | 14.1772 |
| 721 | 890516 | CONTROL | NON IBD | 12.819 | 8.754 | 1.877 | 29.9578 |
| 722 | 890519 | CONTROL | NON IBD | 9.318 | 8.754 | 1.381 | 3.4599 |
| 723 | 890523 | CONTROL | NON IBD | 3.323 | 8.754 | 4.078 | 13.2489 |
| 724 | 890529 | CONTROL | NON IBD | 21.899 | 8.754 | 1.251 | 2.8691 |
| 725 | 900560 | CONTROL | NON IBD | 6.915 | 8.558 | 4.746 | 22.1097 |
| 726 | 900606 | CONTROL | NON IBD | 5.230 | 8.558 | 0.604 | 26.4978 |
| 727 | 900608 | CONTROL | NON IBD | 14.991 | 8.558 | 0.820 | 6.5822 |
| 728 | 910164 | CONTROL | NON IBD | 19.349 | 8.558 | 36.980 | 13.924 |
| 729 | 920551 | CONTROL | NON IBD | 8.731 | 10.984 | 9.250 | 8.0612 |
| 730 | 920552 | CONTROL | NON IBD | 11.369 | 10.984 | 8.989 | 42.5 |
| 731 | 920584 | CONTROL | NON IBD | 5.088 | 10.984 | 1.024 | 14.4786 |
| 732 | 920748 | CONTROL | NON IBD | 9.381 | 11.947 | 29.980 | 49.2873 |
| 733 | 921032 | CONTROL | NON IBD | 10.727 | 11.947 | 0.422 | 4.051 |
| 734 | 930026 | CONTROL | NON IBD | 6.867 | 11.947 | 4.518 | 2.7006 |
| 735 | 930055 | CONTROL | NON IBD | 6.499 | 11.947 | 6.928 | 23.0307 |
| 736 | 930077 | CONTROL | NON IBD | 10.791 | 11.947 | 0.086 | 26.2565 |
| 737 | 930130 | CONTROL | NON IBD | 7.848 | 11.947 | 0.964 | 4.201 |
| 738 | 930138 | CONTROL | NON IBD | 14.654 | 11.947 | 1.406 | 7.5018 |
| 739 | 930230 | CONTROL | NON IBD | 5.886 | 11.947 | 3.112 | 7.4268 |
| 740 | 930252 | CONTROL | NON IBD | 16.048 | 13.486 | 1.667 | 12.378 |
| 741 | 930288 | CONTROL | NON IBD | 11.916 | 13.486 | 0.321 | 5.0262 |
| 742 | 930300 | CONTROL | NON IBD | 12.994 | 13.486 | 1.847 | 10.3525 |
| 743 | 930446 | CONTROL | NON IBD | 13.713 | 13.486 | 3.412 | 13.6909 |
| 744 | 930559 | CONTROL | NON IBD | 9.566 | 11.473 | 0.796 | 29.5436 |
| 745 | 930666 | CONTROL | NON IBD | 5.489 | 11.473 | 8.599 | 17.324 |
| 746 | 930804 | CONTROL | NON IBD | 8.987 | 10.373 | 0.994 | 2.2428 |
| 747 | 930838 | CONTROL | NON IBD | 9.590 | 10.373 | 24.645 | 18.1497 |
| 748 | 930875 | CONTROL | NON IBD | 6.553 | 12.139 | 1.754 | 6.9209 |
| 749 | 930877 | CONTROL | NON IBD | 6.382 | 12.139 | 0.456 | 22.1751 |
| 750 | 930924 | CONTROL | NON IBD | 8.091 | 12.139 | 4.438 | 7.6977 |
| 751 | 930925 | CONTROL | NON IBD | 9.174 | 12.139 | 1.123 | 9.5338 |
| 752 | 930977 | CONTROL | NON IBD | 7.806 | 12.139 | 1.772 | 11.0169 |
| 753 | 86-0034 S | CONTROL | NON IBD | 8.367 | 10.951 | 6.390 | 16.0142 |
| 754 | 86-0074 S | CONTROL | NON IBD | 14.490 | 10.951 | 3.465 | 18.6239 |
| 755 | 86-0085 S | CONTROL | NON IBD | 5.306 | 9.812 | 2.776 | 10.1486 |
| 756 | 86-0126 S | CONTROL | NON IBD | 14.552 | 9.115 | 1.036 | 11.0536 |
| 757 | 87-0005 S | CONTROL | NON IBD | 11.293 | 10.951 | 14.048 | 12.9369 |
| 758 | 87-0022 S | CONTROL | NON IBD | 2.734 | 10.815 | 2.955 | −2.397 |
| 759 | 87-0068 S | CONTROL | NON IBD | 6.064 | 10.815 | 4.183 | 4.9438 |
| 760 | 87-0092 S | CONTROL | NON IBD | 10.544 | 10.951 | 5.361 | 23.9855 |
| 761 | 87-0159 S | CONTROL | NON IBD | 14.959 | 11.895 | 1.408 | 9.736 |
| 762 | 87-0292 S | CONTROL | NON IBD | 8.186 | 9.812 | 2.916 | 7.8651 |
| 763 | 87-0294 S | CONTROL | NON IBD | 6.620 | 9.812 | 1.611 | 10.1612 |
| 764 | 88-0250 S | CONTROL | NON IBD | 4.274 | 11.895 | 1.001 | 4.1642 |
| 765 | 88-0280 S | CONTROL | NON IBD | 9.456 | 10.951 | 5.224 | 75.0296 |
| 766 | 88-0397 S | CONTROL | NON IBD | 6.361 | 12.672 | 2.793 | 5.5443 |
| 767 | 88-0448 S | CONTROL | NON IBD | 8.097 | 10.815 | 3.349 | −4.1947 |
| 768 | 88-0555 S | CONTROL | NON IBD | 10.971 | 10.815 | 15.416 | 1.4981 |
| 769 | 88-0658 S | CONTROL | NON IBD | 10.340 | 10.951 | 4.371 | 9.4899 |
| 770 | 88-0662 S | CONTROL | NON IBD | 18.035 | 9.115 | 1.376 | 4.9228 |
| 771 | 89-0683 S | CONTROL | NON IBD | 12.932 | 11.895 | 4.715 | 10.1466 |
| 772 | 90-0136 S | CONTROL | NON IBD | 12.585 | 10.951 | 10.076 | 23.0614 |
| 773 | 90-0180 S | CONTROL | NON IBD | 9.674 | 10.815 | 1.784 | 146.1423 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 774 | 90-0218 S | CONTROL | NON IBD | 10.166 | 12.672 | 2.099 | 11.2495 |
| 775 | 90-0233 S | CONTROL | NON IBD | 15.872 | 15.179 | 7.081 | 18.9512 |
| 776 | 90-0255 S | CONTROL | NON IBD | 17.951 | 15.179 | 3.666 | 13.5234 |
| 777 | 90-0261 S | CONTRDL | NON IBD | 22.229 | 9.467 | 18.784 | 33.6706 |
| 778 | 90-0286 S | CONTROL | NON IBD | 7.692 | 12.816 | 0.377 | 1.319 |
| 779 | 90-0302 S | CONTROL | NON IBD | 8.590 | 9.812 | 5.422 | 4.137 |
| 780 | 90-0315 S | CONTROL | NON IBD | 19.154 | 9.115 | 5.736 | 7.0458 |
| 781 | 90-0335 S | CONTROL | NON IBD | 9.826 | 9.115 | 2.699 | 5.338 |
| 782 | 90-0703 S | CONTROL | NON IBD | 7.669 | 12.672 | 30.082 | 25.7934 |
| 783 | 90-0734 S | CONTROL | NON IBD | 19.593 | 10.815 | 2.018 | 6.0674 |
| 784 | 91-0267 S | CONTROL | NON IBD | 28.027 | 10.951 | 3.604 | 18.8612 |
| 785 | 91-0484 S | CONTROL | NON IBD | 6.660 | 10.815 | 9.683 | 11.2359 |
| 786 | 92-1001 S | CONTROL | NON IBD | 6.013 | 9.812 | 5.477 | 2.3917 |
| 787 | 92-329 S | CONTROL | NON IBD | 10.821 | 12.816 | 4.353 | 5.7156 |
| 788 | 92-404 S | CONTROL | NON IBD | 90.045 | 9.812 | 3.555 | 3.6638 |
| 789 | 92-407 S | CONTROL | NON IBD | 12.279 | 9.812 | 1.016 | 3.5661 |
| 790 | 92-466 S | CONTROL | NON IBD | 5.104 | 9.812 | 6.863 | 8.549 |
| 791 | 92-702 S | CONTROL | NON IBD | 5.328 | 10.815 | 5.953 | 8.6891 |
| 792 | 92-809 S | CONTROL | NON IBD | 12.164 | 11.895 | 0.831 | 12.6099 |
| 793 | 92-832 S | CONTROL | NON 1BD | 11.973 | 10.951 | 6.217 | 8.5978 |
| 794 | 92-900 S | CONTROL | NON IBD | 10.450 | 10.803 | 2.375 | 20.0000 |
| 795 | 92-9721 S | CONTROL | NON IBD | 5.272 | 10.278 | 3.140 | 11.7276 |
| 796 | 92-988 S | CONTROL | NON IBD | 14.490 | 9.115 | 15.896 | 33.2256 |
| 797 | 93-0487 S | CONTROL | NON IBD | 16.849 | 17.859 | 9.829 | 4.6658 |
| 798 | 93-0509 S | CONTROL | NON IBD | 3.077 | 12.816 | 0.363 | 2.0517 |
| 799 | 93-0654 S | CONTROL | NON IBD | 27.709 | 12.980 | 13.160 | 13.4641 |
| 800 | 93-0741 S | CONTROL | NON IBD | 10.338 | 17.859 | 1.483 | 12.6984 |
| 801 | 93-0746 S | CONTROL | NON IBD | 8.388 | 9.812 | 4.745 | 8.6468 |
| 802 | 93-0768 S | CONTROL | NON IBD | 10.410 | 12.816 | 1.165 | 3.4359 |
| 803 | 93-0996 S | CONTROL | NON IBD | 7.291 | 10.815 | 2.077 | −2.0224 |
| 804 | 93-1001 S | CONTROL | NON IBD | 19.728 | 10.951 | 2.873 | 22.8351 |
| 805 | 93-1010 S | CONTROL | NON IBD | 4.629 | 9.467 | 4.406 | 8.3891 |
| 806 | 93-1039 S | CONTROL | NON IBD | 5.029 | 9.467 | 1.478 | 2.4096 |
| 807 | 94-0017 S | CONTROL | NON IBD | 26.288 | 10.815 | 3.042 | 17.2284 |
| 808 | 94-0083 S | CONTROL | NON IBD | 6.015 | 10.803 | 7.010 | 7.5294 |
| 809 | 94-0095 S | CONTROL | NON IBD | 9.990 | 15.179 | 1.394 | 4.5078 |
| 810 | 94-0104 S | CONTROL | NON IBD | 4.343 | 9.467 | 39.441 | 25.3458 |
| 811 | 94-0143 S | CONTROL | NON IBD | 23.365 | 12.672 | 15.723 | 20.8211 |
| 812 | 94-0181 S | CONTROL | NON IBD | 11.567 | 9.115 | 1.585 | 8.185 |
| 813 | 94-0189 S | CONTROL | NON IBD | 7.967 | 12.672 | 0.220 | 3.695 |
| 814 | 94-0228 S | CONTROL | NON IBD | 13.767 | 10.278 | 2.342 | 10.0392 |
| 815 | 94-0237 S | CONTROL | NON IBD | 13.205 | 11.895 | 7.395 | 20.9384 |
| 816 | 94-0245 S | CONTROL | NON IBD | 9.744 | 12.816 | 2.684 | 11.2848 |
| 817 | 94-0301 S | CONTROL | NON IBD | 15.676 | 12.980 | 3.221 | 14.8173 |
| 818 | 94-0308 S | CONTROL | NON IBD | 9.200 | 9.467 | 2.001 | 11.3788 |
| 819 | 94-0384 S | CONTROL | NON IBD | 14.513 | 17.859 | 1.507 | 12.0428 |
| 820 | 94-0459 S | CONTROL | NON IBD | 30.599 | 10.815 | 8.688 | 12.1348 |
| 821 | 94-0466 S | CONTROL | NON.IBD | 12.752 | 12.980 | 1.527 | 1.6914 |
| 822 | 94-0467 S | CONTROL | NON IBD | 4.686 | 9.467 | 19.113 | 27.9668 |
| 823 | 94-0550 S | CONTROL | NON IBD | 5.314 | 9.467 | 2.554 | 35.4306 |
| 824 | 94-0569 S | CONTROL | NON IBD | 7.551 | 12.672 | 5.684 | 13.2985 |
| 825 | 94-0635 S | CONTROL | NON IBD | 9.333 | 12.816 | 7.079 | 25.5243 |
| 826 | 94-0655 S | CONTROL | NON IBD | 8.939 | 10.238 | 1.987 | 4.4011 |
| 827 | 94-0719 S | CONTROL | NON IBD | 16.347 | 12.980 | 17.939 | 0.6089 |
| 828 | 94-0727 S | CONTROL | NON IBD | 6.171 | 9.467 | 5.929 | 9.5046 |
| 829 | 94-0794 S | CONTROL | NON IBD | 16.836 | 15.179 | 3.807 | 18.8592 |
| 830 | 95-0029 S | CONTROL | NON IBD | 4.101 | 10.278 | 9.122 | 38.5245 |
| 831 | 95-0033 S | CONTROL | NON IBD | 9.959 | 10.278 | 2.324 | 16.5195 |
| 832 | 95-0073 S | CONTROL | NON IBD | 9.888 | 15.179 | 4.261 | 3.4958 |
| 833 | 95-0108 S | CONTROL | NON IBD | 14.400 | 9.467 | 2.330 | 3.1236 |
| 834 | 95-0109 S | CONTROL | NON IBD | 20.086 | 12.980 | 16.321 | 20.0947 |
| 835 | 95-0114 S | CONTROL | NON IBD | 14.503 | 15.179 | 4.935 | 9.4756 |
| 836 | 95-0181 S | CONTROL | NON IBD | 4.114 | 9.467 | 2.479 | 7.0058 |
| 837 | 95-0191 S | CONTROL | NON IBD | 12.697 | 10.803 | 3.206 | 6.9019 |
| 838 | 95-0192 S | CONTROL | NON IBD | 13.943 | 9.467 | 6.173 | 14.4434 |
| 839 | 95-0225 S | CONTROL | NON IBD | 16.826 | 12.980 | 4.229 | 2.7063 |
| 840 | 95-0275 S | CONTROL | NON IBD | 4.469 | 10.238 | 4.968 | 7.1428 |
| 841 | 95-0338 S | CONTROL | NON IBD | 5.858 | 10.278 | 10.159 | 8.9533 |
| 842 | 95-0554 S | CONTROL | NON IBD | 2.855 | 10.803 | 1.977 | 17.3333 |
| 843 | 95-0558 S | CONTROL | NON IBD | 11.891 | 10.238 | 1.758 | 17.8932 |
| 844 | 95-0684 S | CONTROL | NON IBD | 29.657 | 9.467 | 0.862 | 26.1269 |
| 845 | 95-0716 S | CONTROL | NON IBD | 8.006 | 12.980 | 8.977 | 9.4046 |
| 646 | 95-0880 S | CONTROL | NON IBD | 17.029 | 9.467 | 14.742 | 12.0515 |

TABLE 1-continued

ANCA, ASCA-IgA and ASCA-IgG serology data from 851 person database

| COUNT | SAMPLE ID | DIAGNOSIS | IBD CLASS | ANCA ELISA RESULT | ANCA ELISA CUT-OFF | ASCA-IgA RESULT (EU) | ASCA-IgG RESULT (EU) |
|---|---|---|---|---|---|---|---|
| 847 | 95-0887 S | CONTROL | NON IBD | 7.095 | 12.980 | 10.992 | 30.9201 |
| 848 | 95-1012 S | CONTROL | NON IBD | 13.998 | 12.980 | 9.420 | 30.5818 |
| 849 | 95-1038 S | CONTROL | NON IBD | 15.159 | 17.859 | 7.097 | 26.2295 |
| 850 | 95-1077 S | CONTROL | NON IBD | 14.066 | 17.859 | 2.858 | 4.7919 |
| 851 | 96-0107 S | CONTROL | NON IBD | 9.197 | 10.278 | 3.339 | 7.9215 |

The individuals described in Table 1 were classed in one of several disease or control categories. As shown in Table 2, of the 851 total patients, 433 (50.88%) were in the IBD category and 418 (49.12%) were in the Non-IBD category. All serum samples were tested by neutrophil ELISA and for immunoglobulin G and immunoglobulin A antibodies to mannan from *Saccharomyces cerevisiae uvarum* as described in Example I. Neutrophil ELISA positive samples were additionally analyzed by immunofluorescence assay with neutrophil substrate, followed by DNase treatment for immunofluorescence positive samples that show a perinuclear pattern. No other measurements were made on the samples.

TABLE 2

Inflammatory Bowel Disease Database

| Disease or Control Category | Number of Patients | Percent of Total |
|---|---|---|
| IBD Category | | |
| Crohn's disease* | 218 | 25.62 |
| Ulcerative colitis* | 212 | 24.91 |
| Ulcerative colitis/PSC* | 3 | 0.35% |
| IBD Subtotal | 433 | 50.88 |
| Non-IBD category | | |
| Disease control* | 60 | 7.05 |
| Non-IBD* | 35 | 4.11 |
| IBS* | 22 | 2.59 |
| Wegener's granulomatosis* | 1 | 0.12 |
| Control | 300 | 35.35 |
| Non-IBD subtotal | 418 | 49.12 |
| Total | 851 | 100 |

*verified by colonoscopy, radiology and/or histology

B. Simultaneous Variation of ANCA, ASCA-IgA and ASCA-IgG Cut-Off Values

The three different ELISA cut-off values for ANCA reactivity, ASCA-IgA reactivity and ASCA-IgG reactivity were varied simultaneously. Base cut-off values were determined as follows:

To determine the base cut-off value for ANCA reactivity, a panel of twenty verified negative control samples was used with a calibrator with a defined ELISA Unit (EU) value. The base positive/negative cut-off for each ELISA run was defined as the optical density (OD) of the Calibrator minus the mean (OD) value for the panel of twenty negatives (plus 2 standard deviations) times the EU value of the Calibrator. The base cut-off value for ANCA reactivity was therefore about 10 to 20 EU, with any patient sample having an average EU value greater than the base cut-off marked as ELISA positive for ANCA reactivity. Similarly, a patient sample having an average EU value is less than or equal to the base cut-off was determined to be negative for ANCA reactivity.

To determine the base cut-off value for ASCA-IgA and ASCA-IgG, single point calibrators having fixed EU values were used. OD values for patient samples were compared to the OD value for the Calibrators and multiplied by the Calibrator assigned values. The base cut-off value for the ASCA-IgA ELISA was 20 EU. The base cut-off value for the ASCA-IgG ELISA was 40 EU.

Using this existing set of test data for 851 patients having IBD status determined by colonoscopy or radiology or both or who were asymptomatic controls, the three cut-off values were simultaneously adjusted to observe the effects on clinical parameters: sensitivity, specificity, negative predictive value, positive predictive value, and overall agreement. In particular, design of Experiments (DOE) methodology was used to simultaneously vary the three cut-off ELISA values and to determine the effects on the resulting clinical parameters of sensitivity, specificity, negative predictive value, positive predictive value and overall agreement. The DOE methodology is advantageous in that variables are tested in a nested array requiring fewer runs and identifying cooperative interactions among the three cut-off variables. Optimization software DOE Keep It Simple Statistically (KISS) was obtained from Air Academy Associates (Colorado Springs, Colo.) and used to assign experimental runs and perform the simultaneous equation calculations.

Cut-off values were varied as set forth in Table 3 below:

TABLE 3

Ranges of ANCA, ASCA-IgA and ASCA-IgG cut-off values

| ELISA | Low Cut-off Value | Standard Cut-off Value | High Cut-off Value |
|---|---|---|---|
| ANCA | 0.5X Standard | 1.0X Standard | 1.5X Standard |
| ASCA-IgA | 10 EU | 20 EU | 30 EU |
| ASCA-IgG | 20 EU | 40 EU | 60 EU |

A three variable (ANCA cut-off, ASCA-IgA cut-off, ASCA-IgG cut-off) and three level (low, middle, and high; see Table 3) central composite (CCD) factorial design experiment was conducted as follows. In each experiment listed, the cut-off values for each of the three ELISA tests were set as shown in the first column of Table 4. Analysis using the KISS program was made with all first, second and third order variables operable. The first experiment shown in row 1 of Table 4, for example, indicates a cut-off value of ANCA=0.5, ASCA-IgA=10, and ASCA-IgG=20. By comparison with these assigned cut-off values, the test results determined for all of the 851 samples in the data base were assigned as true positive, true negative, false positive, or false negative. Using these results and the clinically defined diagnosis, sensitivity, specificity, overall agreement, positive predictive value, and negative predictive value were calculated. Using the DOE KISS program, optimized sets of cut-off values for selected clinical parameters were calculated.

The clinical parameter results for each set of three cut-off variables are shown in Table 4. Although these results are the calculated points determined by the experimental design, clinical parameter results for any other set of cut-offs within the cut-off boundaries also can be calculated. The three dimensional test box determined by the extremes of the three variables defines the region in which testing was conducted. These results show that there is a continuum of solutions of clinical responses within the boundaries of the cut-off values and that the DOE methodology can be used to determine the sets of cut-off values which present the most useful clinical parameters for a particular patient population.

TABLE 4

Clinical Parameter Results from Simultaneous Variation of ANCA, ASCA-IgA, and ASCA-IgG cut-off values X, Y, and Z in a population with 50% disease prevalence

| Cut-offs* | % Sens. | % Spec. | % Overall Agreement | % PPV | % NPV |
|---|---|---|---|---|---|
| 0.5/10/20 | 96.3 | 13.6 | 55.7 | 60.5 | 78.1 |
| 0.5/10/60 | 95.2 | 14.8 | 55.7 | 53.6 | 74.7 |
| 0.5/30/20 | 96.1 | 14.4 | 55.9 | 53.8 | 77.9 |
| 0.5/30/60 | 94.9 | 16.3 | 56.3 | 54.0 | 75.6 |
| 1.5/10/20 | 81.3 | 64.6 | 73.1 | 70.4 | 76.9 |
| 1.5/10/60 | 77.1 | 75.4 | 76.3 | 76.4 | 76.1 |
| 1.5/36/20 | 78.5 | 70.8 | 74.4 | 73.6 | 76.1 |
| 1.5/30/60 | 69.5 | 86.1 | 77.7 | 83.7 | 73.2 |
| 1.0/20/40 | 82.2 | 67.3 | 74.9 | 72.2 | 78.5 |
| 1.0/20/40 | 82.2 | 67.3 | 74.9 | 72.2 | 78.5 |
| 0.5/20/40 | 94.9 | 16.3 | 56.3 | 54.0 | 75.6 |
| 1.5/20/40 | 74.1 | 83.5 | 78.7 | 82.3 | 75.7 |
| 1.0/10/40 | 85.0 | 61.0 | 73.2 | 69.3 | 79.7 |
| 1.0/30/40 | 80.6 | 57.4 | 69.2 | 66.2 | 74.1 |
| 1.0/20/20 | 85.2 | 57.7 | 71.7 | 67.6 | 79.0 |
| 1.0/20/60 | 81.8 | 67.5 | 74.7 | 72.2 | 78.1 |

*ANCA/ASCA-IgA/ASCA-IgG cut-offs

The maximum possible sensitivity, specificity, negative predictive value, positive predictive value and overall agreement within the range of ANCA values (0.5× to 1.5× standard); ASCA-IgA values (10 To 30 ELISA units) and ASCA-IgG values (20 to 60 ELISA units) were determined with the entire 851 person database having an IBD disease prevalence of 50%. The results are shown in Table 5.

TABLE 5

Maximum possible clinical parameters in a population having an IBD disease prevalence of 50%

| Clinical Parameters (N = 851) | Maximum possible correlation | Cut-off values ANCA/ASCA-IgA/ASCA-IgG |
|---|---|---|
| Sensitivity | 96.61% | 0.50; 10.00; 20 |
| Specificity | 87.57% | 1.50; 24.48; 60 |
| Negative predictive value | 80.25 | 0.90; 14.21; 20 |
| Positive predictive value | 84.54 | 1.50; 26.10; 60 |
| Overall agreement | 79.57% | 1.46; 20.42; 60 |

The results shown in Table 5 give the maximum possible clinical parameters within the ranges of cut-off values explored in a population with an IBD disease prevalence of 50%. For example, the highest possible sensitivity is 96.61% and is obtained with an ANCA cut-off of 0.5, an ASCA-IgA cut-off of 10 EU, and an ASCA-IgG cut-off of 20 EU. At this high sensitivity, specificity is reduced, being only 13.16% at this cut-off. These results demonstrate that ANCA, ASCA-IgA and ASCA-IgG values can be determined to give maximum sensitivity, but that other cut-off values are needed to yield maximum specificity.

C. Determination of ANCA, ASCA-IgA and ASCA-IgG Cut-Off Values for High Sensitivity Sensitivity is the fraction of all those with IBD who are diagnosed positive for IBD with the first step assay. Values were selected that produced a high sensitivity (90.3%) while still maintaining a relatively high specificity. In particular, 90.3% sensitivity was achieved by setting the ANCA cut-off at 0.7 multiplied by two standard deviations above the background value of ANCA-negative UC sera, ASCA-IgA cut-off at 12 EU and the ASCA-IgG cut-off at 60 EU (see Table 6). These cut-offs are distinct from the cut-offs used in the UC*Dx-1 and CD*Dx-1 assays, which are 1.0, 20, and 60, respectively.

TABLE 6

Evaulation of results with high sensitivity assay having ANCA cut-off = 0.7, ASCA-IgA cut-off = 12 EU and an ASCA-IgG cut-off = 60 EU.

|  | True IBD Positive | True IBD Negative | Totals |
|---|---|---|---|
| First step assay positive | 391 | 262 | 653 |
| First Step assay negative | 42 | 156 | 198 |
| Totals | 433 | 418 | 851 |

With an ANCA cut-off of 0.7 multiplied by two standard deviations above the background value of ANCA-negative UC sera, an ASCA-IgA cut-off of 12 EU, and an ASCA-IgG cut-off of 60 EU, the specificity was determined to be 37.3%. Using these cut-off values and the entire 851 patient database (having an IBD disease prevalence of 50%), the negative predictive value was 78.8%, the positive predictive value was 59.9%, and the overall agreement was 64.3%. These data also can be modeled for an IBD prevalence of 15%, which represents the approximate IBD disease prevalence in a gastroenterologist's office population (see Table 7). In a population having an IBD prevalence of 15%, an ANCA cut-off of 0.7 multiplied by two standard deviations above the background value of ANCA-negative UC sera, an ASCA-IgA cut-off of 12 EU and an ASCA-IgG cut-off of 60 EU resulted in a negative predictive value of 95.6%, a positive predictive value of 20.3%, and overall agreement of 45.3%. The calculated performance at 15% IBD prevalence was confirmed by randomly choosing patients from the n=851 database to construct and analyze a new database (n=277) that had a 15% IBD prevalence.

TABLE 7

Clinical parameters with 50%, 15% and 1% IBD disease prevalence for assays run with an ANCA cut-off = 0.7, an ASCA-IgA cut-off = 12 EU and an ASCA-IgG cut-off = 60 EU

| Clinical parameter | Disease prevalence | | |
|---|---|---|---|
| | 50% | 15% | 1% |
| Sensitivity | 90.3% | 90.3% | 90.3% |
| Specificity | 37.3% | 37.3% | 37.3% |
| Negative predictive value | 78.8% | 95.6% | 99.7% |
| Positive predictive value | 59.9% | 20.3% | 1.43% |
| Overall agreement | 64.3% | 45.3% | 37.8% |

EXAMPLE III

Use of the Sensitive 'First Step' Method In Combination With Subsequent, Specific Diagnostic Assays This example demonstrates that the "First Step" diagnostic method can be used in combination with subsequent, specific diagnostic assays such as the UC*Dx-1 and CD*Dx-1 assays.

Samples which were positive by "First Step" analysis (including true positive and false positive samples) were subsequently tested by the UC*Dx-1 and CD*Dx-1 assays, which are specific for ulcerative colitis and Crohn's disease, respectively. The results are shown in Table 8.

TABLE 8

Results of reflex of samples positive by "First Step" diagnosis to the UC*Dx-1 and CD*Dx-1 assays

| | True IBD Positive | True IBD Negative | Totals |
|---|---|---|---|
| CD*Dx-1 and/or UC*Dx-1 Positive | 287 | 38 | 325 |
| CD*Dx-1 and/or UC*Dx-1 Negative | 146 | 380 | 526 |
| Totals | 433 | 418 | 851 |

Together, reflex of samples positive by "First Step" analysis to the UC*Dx-1 and CD*Dx-1 performs with 66.3% sensitivity, 90.9% specificity, 72.2% negative predictive value, 88.3% positive predictive value and 78.4% overall agreement. These results indicate that subsequent analysis of positive samples can amplify on the initial "First Step" result. These results indicate that the "First Step" diagnostic can be used, if desired, in combination with a subsequent, more specific diagnostic method.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A highly sensitive method of diagnosing inflammatory bowel disease (IBD) in an individual, comprising the steps of:

(a) isolating a sample from said individual;

(b) determining by non-histological means whether said sample is positive for anti-neutrophil cytoplasmic antibodies (ANCA);

(c) determining whether said sample is positive for anti-*Saccharomyces cerevisiae* immunoglobulin A (ASCA-IgA);

(d) determining whether said sample is positive for anti-*Saccharomyces cerevisiae* immunoglobulin G (ASCA-IgG); and (e) diagnosing said individual as having IBD when said sample is positive for ANCA, ASCA-IgA or ASCA-IgG, and diagnosing said individual as not having IBD when said sample is negative for ANCA, ASCA-IgA and ASCA-IgG, provided that said method does not include histological analysis of neutrophils.

2. The method of claim 1, said method consisting of steps (a), (b), (c), (d) and (e).

3. The method of claim 1, wherein ANCA, ASCA-IgA and ASCA-IgG positivity are determined using an enzyme-linked immunosorbent assay (ELISA).

4. A highly sensitive method of diagnosing IBD in an individual, comprising the steps of:

(a) isolating a sample from said individual;

(b) determining by non-histological means whether said sample has an ANCA level above an ANCA cut-off value (X);

(c) determining whether said sample has an ASCA-IgA level above an ASCA-IgA cut-off value (Y);

(d) determining whether said sample has an ASCA-IgG level above an ASCA-IgG cut-off value (Z); and (e) diagnosing said individual as having IBD when said ANCA level is above X, said ASCA-IgA level is above Y, or said ASCA-IgG level is above Z, and diagnosing said individual as not having IBD when said ANCA level is below X, said ASCA-IgA level is below Y.

and said ASCA-IgG value is below Z, wherein X, Y, and Z are independently selected to achieve an optimized clinical parameter selected from the group consisting of: sensitivity, specificity, negative predictive value, positive predictive value and overall agreement, provided that said method does not include histological analysis of neutrophils.

5. The method of claim 4, wherein X, Y and Z are independently selected such that the sensitivity of diagnosing an individual with IBD is at least about 70%.

6. The method of claim 5, wherein X, Y and Z are independently selected such that the specificity of diagnosing an individual with IBD is 30–60%.

7. The method of claim 6, wherein X, Y and Z are independently selected such that the negative predictive value in a population having an IBD disease prevalence of about 15% is at least about 90%.

8. The method of claim 7, wherein said negative predictive value is at least about 95%.

9. The method of claim 4, wherein X, Y and Z are independently selected such that the sensitivity of diagnosing an individual with IBD is at least about 90%.

10. The method of claim 9, wherein X, Y and Z are independently selected such that the specificity of diagnosing an individual with IBD is 20–60%.

11. The method of claim 10, wherein X, Y and Z are independently selected such that the negative predictive value in a population having an IBD disease prevalence of about 15% is at least about 90%.

12. The method of claim 11, wherein said negative predictive value is at least about 95%.

13. The method of claim 12, wherein X, Y and Z are independently selected such that the sensitivity of diagnosing an individual with IBD is about 90%, the specificity is about 37% and the negative predictive value in a population having an IBD disease prevalence of about 15% is about 95%.

14. The method of claim 4, wherein X, Y and Z are independently selected such that the negative predictive value in a patient population having an IBD disease prevalence of about 15% is at least about 95%.

15. The method of claim 4, said method consist of steps (a), (b), (c), (d) and (e).

16. The method of claim 4, wherein said ANCA level, ASCA-IgA level and ASCA-IgG level each is determined using an ELISA.

17. A highly sensitive method of diagnosing IBD in an individual, comprising the steps of:
 (a) isolating a sample from said individual;
 (b) contacting an appropriate dilution of said sample with antigen specific for ANCA under conditions suitable to form a first complex of ANCA and antigen specific for ANCA to determine by non-histological means the amount of said first complex;
 (c) contacting an appropriate dilution of said sample with antigen specific for ASCA under conditions suitable to form a second complex of ASCA and antigen specific for ASCA;
 (d) contacting said second complex with anti-immunoglobulin A antibody to determine the amount of ASCA-IgA containing second complex;
 (e) contacting said second complex with anti-immunoglobulin G antibody to determine the amount of ASCA-IgG containing second complex;
 (f) diagnosing said individual as having IBD when the amount of first complex formed is greater than an ANCA cut-off value (X),
 the amount of IgA-containing second complex formed is greater than an ASCA-IgA cut-off value (Y), or
 the amount of IgG-containing second complex formed is greater than an ASCA-IGG cut-off value (Z),
 and diagnosing said individual as not having IBD when
 the amount of first complex formed is less than X,
 the amount of IgA-containing second complex formed is less than Y, and
 the amount of IgG-containing second complex formed is less than Z,
 wherein X, Y, and Z are independently selected to achieve an optimized clinical parameter selected from the group consisting of: sensitivity, specificity, negative predictive value, positive predictive value and overall agreement,
 provided that said method does not include histological analysis of neutrophils.

18. The method of claim 17, wherein said sample is a serum sample.

19. The method of claim 17, wherein said sample is a saliva sample.

20. The method of claim 17, wherein said antigen specific for ANCA is fixed neutrophils.

21. The method of claim 17, wherein said antigen specific for ASCA is yeast cell wall phosphopeptidomannan (PPM).

22. The method of claim 21, wherein said yeast cell wall PPM is prepared from strain ATCC #38926.

23. A highly efficient method of analyzing multiple samples for IBD, comprising the steps of:
 (a) first assaying all samples by non-histological means for the presence or absence of ANCA;
 (b) next assaying only ANCA-negative samples for the presence or absence of ASCA-IgA;
 (c) next assaying only ANCA-negative and ASCA-IgA-negative samples for the presence or absence of ASCA-IgG,
 wherein the presence of ANCA, ASCA-IgA or ASCA-IgG in a sample is indicative of IBD and
 wherein the absence of pANCA, ASCA-IgA and ASCA-IgG is indicative of the absence of IBD.

24. The method of claim 23, wherein the presence of ANCA, ASCA-IgA and ASCA-IgG is determined using an ELISA.

* * * * *